United States Patent
Beaudet et al.

(10) Patent No.: US 7,977,057 B2
(45) Date of Patent: *Jul. 12, 2011

(54) DETECTION OF IMMOBILIZED NUCLEIC ACID

(75) Inventors: Matthew Beaudet, Eugene, OR (US); Gregory Cox, Portland, OR (US); Stephen Yue, Eugene, OR (US)

(73) Assignee: Life Technologies Corporation, Carslbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/771,897

(22) Filed: Apr. 30, 2010

(65) Prior Publication Data

US 2010/0216665 A1   Aug. 26, 2010

Related U.S. Application Data

(63) Continuation of application No. 10/956,868, filed on Sep. 30, 2004, now Pat. No. 7,727,716.

(60) Provisional application No. 60/507,630, filed on Sep. 30, 2003.

(51) Int. Cl.
*C12Q 1/68* (2006.01)
*C07H 21/00* (2006.01)
*C07D 209/04* (2006.01)

(52) U.S. Cl. ........... 435/6; 536/23.1; 536/26.6; 548/469

(58) Field of Classification Search ..... 435/6; 536/23.1, 536/26.6; 548/469
See application file for complete search history.

(56) References Cited

U.S. PATENT DOCUMENTS 4,883,867 A   11/1989 Lee et al.
(Continued)

FOREIGN PATENT DOCUMENTS

WO   WO-94/24213   10/1994
(Continued)

OTHER PUBLICATIONS

Matselyukh et al. (J. Biochem. Biophys. Methods 57 (2003) 35-43).*
(Continued)

*Primary Examiner* — Jezia Riley
(74) *Attorney, Agent, or Firm* — Life Technologies Corporation; James K. Blodgett

(57) ABSTRACT

The present invention provides methods for determining the presence of immobilized nucleic acid employing unsymmetrical cyanine dyes that are derivatives of thiazole orange, a staining solution and select fluorogenic compounds that are characterized as being essentially non-genotoxic. The methods comprise immobilizing nucleic acid, single or double stranded DNA, RNA or a combination thereof, on a solid or semi solid support, contacting the immobilized nucleic acid with an unsymmetrical cyanine dye compound and then illuminating the immobilized nucleic acid with an appropriate wavelength whereby the presence of the nucleic acid is determined. The cyanine dye compounds are typically present in an aqueous staining solution comprising the dye compound and a tris acetate or tris borate buffer wherein the solution facilitates the contact of the dye compound and the immobilized nucleic acid. Typically the solid or semi-solid support is selected from the group consisting of a polymeric gel, a membrane, an array, a glass bead, a glass slide, and a polymeric microparticle. Preferably, the polymeric gel is agarose or polyacrylamide. The methods employing the non-genotoxic compounds represent an improvement over commonly used methods employing ethidium bromide wherein the present methods retain the advantages of ethidium bromide, ease of use and low cost, but without the disadvantageous, known mutagen requiring special handling and waste procedures.

11 Claims, 9 Drawing Sheets

U.S. PATENT DOCUMENTS

| | | | |
|---|---|---|---|
| 4,957,870 | A | 9/1990 | Lee et al. |
| 5,321,130 | A | 6/1994 | Yue et al. |
| 5,436,134 | A | 7/1995 | Haugland et al. |
| 5,534,416 | A | 7/1996 | Millard et al. |
| 5,582,702 | A | 12/1996 | Cabilly et al. |
| 5,656,449 | A | 8/1997 | Yue |
| 5,658,751 | A | 8/1997 | Yue et al. |
| 5,863,753 | A | 1/1999 | Haugland et al. |
| 5,865,874 | A | 2/1999 | Trainer |
| 5,929,227 | A | 7/1999 | Glazer et al. |
| 6,379,516 | B1 | 4/2002 | Cabilly et al. |
| 6,562,213 | B1 | 5/2003 | Cabilly et al. |
| 7,727,716 | B2 * | 6/2010 | Beaudet et al. ............... 435/6 |
| 2002/0112960 | A1 | 8/2002 | Cabilly et al. |
| 2002/0134680 | A1 | 9/2002 | Cabilly et al. |
| 2010/0227331 | A1 | 9/2010 | Beaudet et al. |

FOREIGN PATENT DOCUMENTS

| | | |
|---|---|---|
| WO | WO-96/34276 | 10/1996 |
| WO | WO-97/41070 | 11/1997 |
| WO | WO-9942620 A2 | 8/1999 |

OTHER PUBLICATIONS

McIntosh (Analytical Chemistry, vol. 72, No. 21, Nov. 1, 2000).*
U.S. Appl. No. 10/956,868, "Notice of Allowance Mailed on Feb. 10, 2009".
U.S. Appl. No. 10/956,868, "Notice of Allowance", Oct. 2, 2008.
U.S. Appl. No. 10/956,868, "Office Action mailed May 25, 2007".
U.S. Appl. No. 10/956,868, "Office Action Mailed Jun. 25, 2009".
U.S. Appl. No. 10/956,868, "Office Action mailed Jul. 3, 2008".
U.S. Appl. No. 10/956,868, "Office Action mailed Oct. 26, 2007".
U.S. Appl. No. 10/956,868, "Office Action mailed on Jan. 14, 2010".
U.S. Appl. No. 10/956,868, "Response to May 25, 2007 Office Action", Filed Aug. 10, 2007.
U.S. Appl. No. 10/956,868, "Response to Jul. 3, 2008 Office Action", Filed Aug. 28, 2008.
U.S. Appl. No. 10/956,868, "Response to Oct. 26, 2007 Office Action", Filed Feb. 26, 2008.
U.S. Appl. No. 10/956,868, "Response to Rest. Req.", Filed Mar. 12, 2007.
U.S. Appl. No. 10/956,868, "Restriction Req. mailed Jan. 12, 2007".
U.S. Appl. No. 12/778,774, "Office Action Mailed Jul. 22, 2010".
U.S. Appl. No. 12/778,774, "Response to Office Action Mailed Jul. 22, 2010, filed Jan. 19, 2011".
2006-534241, "Office action mailed Jun. 24, 2010".
2006-534241, "Response to Office Action mailed Jun. 24, 2010", Filed on Nov. 16, 2010.
Amacher, David E. et al., "Point mutations at the thymidine kinase locus in L5178Y mouse lymphoma cells II. Test validation and interpretation", Mutation Research vol. 72, No. 3 Aug. 1980, 447-474.
Ames, Bruce N. et al., "Methods for detecting carcinogens and mutagens with the Salmonella/mammalian-microsome mutagenicity test.", Mutation Research vol. 31, No. 6 Dec. 1975, 347-364.
Axton, R A. et al., "Use of stable dye-DNA intercalating complexes to detect cystic fibrosis mutations", Molecular and Cellular Probes vol. 8 Jun. 8, 1994, 245-50.
Brooker, L G. et al., "Color and consitution. V. The absorption of unsymmetrical cyanines. Resonance as a basis for a classification of dyes", Journal of the American Chemical Society vol. 64, Communication No. 833 From the Kodak Research Laboratories Feb. 1942, 199-210.
Brooker, L.G.S. et al., "Color and constitution. X. Absorption of the Merocyanines", Journal of the American Chemical Society vol. 73, Communication No. 1397 from the Kodak Research Laboratories. 1951, 5332-5350.
Clive, D. et al., "Validation and characterization of the L5178Y/ TK+/− mouse lymphoma mutagen assay system", Mutation Research vol. 59, No. 1 1979, 61-108.
Clive, D. et al., "Laboratory procedure for assessing specific locus mutations at the TK locus in cultured L5178Y mouse lymphoma cells", Mutation Research vol. 31, No. 1 1975, 17-29.
Clive, Donald W. et al., "Guide for performing the mouse lymphoma assay for mammalian cell mutagenicity", Mutation Research vol. 189, No. 2 1987, 143-156.
Deligeorgiev, et al., "Preparation of Monomethine Cyanine Dyes for Nucleic Acid Detection", Dyes and Pigments 1998, vol. 37, No. 3, pp. 205-211 1998, 205-211.
EP 04789513, "Examination Report mailed Feb. 14, 2008".
EP 04789513, "Examination Report mailed Feb. 26, 2007".
EP 08158255, "EPO Search Report", Oct. 1, 2008.
EP 08158255, "Examination Report mailed Mar. 11, 2009".
Eriksson, Maja et al., "Groove-Binding Unsymmetrical Cyanine Dyes for Staining of DNA: Dissociation Rates in Free Solution and Electrophoresis Gels", Nucleic Acids Research vol. 31 No. 21 2003, 6235-6242.
Evans, H. J., "Cytological method for detecting chemical mutagens", Chemical Mutagens, Principles and Methods for their Detection. vol. 4 1976, 1-29.
Fukunaga, Masahito et al., "Production of frameshift mutations in Salmonella by phenanthridium derivatives: enzymatic activation and photoaffinity labeling", Mutatation Research vol. 127, No. 1 1984, 31-37.
Furniss, Brian S. et al., "Resolution of Racemates", Vogel's Textbook of Practical Organic Chemistry Fifth Ed, Longman Group UK Ltd., Essex 1989, 809-823.
Haab, Brian B. et al., "Single molecule fluorescence burst detection of DNA fragments separated by capillary electrophoresis", Analytical Chemistry vol. 67 No. 18 Sep. 15, 1995, 3253-3260.
Heller, A., "Electrical Wiring of Redox Enzymes", Acc. Chem. Res. vol. 23, No. 5 1990, 128-134.
Kerckaert, G A. et al., "A comprehensive protocol for conducting the Syrian hamster embryo cell transformation assay at pH 6.70.", Mutation Research vol. 356, No. 1 Sep. 21, 1996, 65-84.
Le Pecq, Jean-Bernard et al., "A new fluorometric method for RNA and DNA determination", Analytical Biochemistry vol. 17, No. 1 1966, 100-107.
Levin, David E. et al., "A new Salmonella tester strain (TA102) with A X T base pairs at the site of mutation detects oxidative mutagens.", Proceedings of the National Academy of Sciences (PNAS) vol. 79, No. 23 Dec. 1, 1982, 7445-7449.
Maron, Dorothy M. et al., "Revised methods for the Salmonella mutagenicity test", Mutation Research vol. 113, No. 3-4 1983, 173-215.
Matselyukh, et al., "Interaction of cyanine dyes with nucleic acids : XXXI. using of polymethine cyanine dyes for the visualisation of DNA in agarose gels", Journal of Biochemical and Biophysical Methods vol. 57, No. 1 2003, 35-43.
McCann, Joyce, "Detection of carcinogens as mutagen in the Salmonella/microsomes test: assay of 300 chemicals", Proceeedings of the National Academy of Sciences (PNAS) vol. 72, No. 12 Dec. 15, 1975, 5135-5139.
McIntosh, Sara L. et al., "Fluorescence Lifetime for On-the-Fly Multiplex Detection of DNA Restriction Fragments in Capillary Electropheresis", Analytical Chemistry vol. 72 No. 21 Nov. 1, 2000, 5444-5449.
Nygren, Jan et al., "The Interaction between the Fluorescent Dye Thiazole Orange and DNA", Biopolymer vol. 46 1998, 39-51.
PCT/US04/032693, "International Preliminary Report on Patentability, date of issuance Apr. 3, 2006".
PCT/US04/032693, "PCT ISR", Feb. 7, 2005.
PCT/US04/032693, "PCT Written Opinion", Feb. 7, 2005.
Quesada, M A. et al., "High-sensitivity DNA detection with a laser-excited confocal fluorescence gel scanner", Biotechniques vol. 10 No. 5 May 1991, 616-625.
Rye, Hays S. et al., "High-sensitivity two-color detection of double-stranded DNA with a confocal fluorescence gel scanner using ethidium homodimer and thiazole orange", Nucleic Acids Res vol. 19 No. 2 1990, 327-333.
Rye, Hays S. et al., "Picogram detection of stable dye-DNA intercalation complexes with two-color laser-excited confocal fluorescence gel scanner", Methods in Enzymology vol. 237 1993, 414-431.
Rye, Hays S. et al., "Stable Fluorescent Complexes of Double-Stranded DNA With Bis-Intercalating Asymmetric Cyanine Dyes:

Properties and Applications", *Nucleic Acids Research* vol. 20 No. 11, Oxford University Press 1992, 2803-2812.

Singer, Victoria L. et al., "Comparison of SYBR Green I nucleic acid gel stain mutagenicity and ethidium bromide mutagenicity in the *Salmonella*/mammalian microsome reverse mutation assay (Ames test).", *Mutation Research* vol. 439, No. 1 Feb. 2, 1999, 37-47.

Skeidsvoll, Jarle et al., "Analysis of Double-Stranded DNA by Capillary Electrophoresis with Laser-Induced Flurorescence Detection using Monomeric Dye SYBR Green I", *Analytical Biochemistry* vol. 231, Academic Press, Inc Nov. 1, 1995, 359-365.

Srinivasan, Kannan et al., "Enhanced Detection of PCR products through use of TOTO and YOYO Intercalating Dyes with Laser Induced Fluorescence—Capiliary Electrophoresis", *Applied and Theoretical Electrophoresis* vol. 3 No. 5 Mar. 8, 1993, 235-239.

Stratagene Catalog, Gene Characterization Kits, *Stratagene Catalog* 1988, 39.

Svanvik, Nicke et al., "Light-Up Probes: Thiazole Orange-Conjugated Peptide Nucleic Acid for Detection of Target Nucleic Acid in Homogeneous Solution", *Analytical Biochemistry* vol. 281 2000, 26-35.

Timtcheva, I. et al., "New Asymmetric Monomethine Cyanine Dyes for Nucleic-Acid Labelling: Absorption and Fluorescence Spectral Characteristics", *Journal of Photochemistry and Photobiology A: Chemistry* 130 2000, 7-11.

Waring, M. J., "Complex formation between ethidium bromide and nucleic acids", *The Journal of Molecular Biology* vol. 13, No. 1 1965, 269-282.

Wilke, Werner W. et al., "Use of thiazole orange homodimer as an alternative to ethidium bromide for DNA detection in agarose gels", *Modern Pathology* vol. 7 No. 3 Apr. 7, 1994, 385-387.

Woolley, Adam T. et al., "High-speed DNA genotyping using microfabricated capillary array electrophoresis chips", *Analytical Chemistry* vol. 69 No. 1 Jun. 1, 1997, 2181-2186.

Yamasaki, Hiroshi, "Preface", *Mutation Research/Fundamental and Molecular Mechanisms of Mutagenesis* vol. 356, No. 1 Sep. 21, 1996, 1-3.

Zhu, Huiping et al., "High-sensitivity capillary electrophoresis of double-stranded DNA fragments using monomeric and dimeric fluorescent intercalating dyes", *Analytical Chemistry* vol. 66, No. 13 Jul. 1, 1994, 1941-1948.

U.S. Appl. No. 12/778,774, "Office action mailed on Mar. 30, 2011".

CA 2,540,508, "Office action Mailed May 2, 2011".

* cited by examiner

E-Gel 48 2% Compound 1

DETECTION OF IMMOBILIZED NUCLEIC ACID

CROSS-REFERENCE TO RELATED APPLICATIONS

This application is a continuation of U.S. patent application Ser. No. 10/956,868, filed Sep. 30, 2004, which claims priority to U.S. Provisional Patent Application Ser. No. 60/507,630, filed Sep. 30, 2003, the contents of which are hereby incorporated herein by reference in their entirety.

FIELD OF THE INVENTION

The present invention relates to unsymmetrical cyanine monomer compounds that provide a detectable fluorescent signal when complexed with nucleic acid polymers. The invention has applications in the fields of molecular biology and fluorescence based assays.

BACKGROUND OF THE INVENTION

The detection of immobilized nucleic acid, especially nucleic acid separated on gels, is a widely used method. Numerous chromophores and dyes exist for the detection of nucleic acids however, despite its relatively high detection limit, ethidium bromide is still one of the most commonly used nucleic acid detection reagents due in part to its ease of use and low cost.

Ethidium bromide is easy to use as a nucleic acid gel stain because the nucleic acid can be pre- or post-stained and requires no special equipment for visualization beyond a UV light source. Ethidium bromide is excited by UV light, less than 400 nm, and has an emission spectra of about 620 nm when bound to DNA. Thus, the stained gels can be excited by an ultraviolet transilluminator, which typically has a light wavelength of about 300 nm, and the excited ethidium bromide-DNA complex gel photographed using black and white Polaroid film. Despite the convenience of ethidium bromide, the compound posses some significant disadvantages; namely that the compound is a known mutagen and carcinogen which requires special handling and waste disposal procedures. Ethidium bromide has been shown to inhibit replication in several organisms by interfering with both DNA and RNA synthesis, to be mutagenic in an Ames test and to cause frameshift mutations in bacteria (M. J. Waring J. Mol. Biol. 13 (1965) 269-282; McCann et al. PNAS 72 (1975) 5135-5139; Singer et al. Mutation Research 439 (1999) 37-47). This is because ethidium bromide is believed to intercalate dsDNA and thus causes errors during replication (Fukunaga et al. Mutation Research 127 (1984) 31-37).

Due to these limitations of ethidium bromide, we wanted to develop an improved method for detecting immobilized nucleic acid that retained the advantages of ethidium bromide, ease of use and low cost, but overcame the limitations of ethidium bromide. Thus, to satisfy this criteria the method and subsequent dye must 1) be relatively easy to synthesize in large quantities (low cost), 2) be present in the staining solution at a relatively low concentration (low cost), 3) excited by UV light (ease of use so that the nucleic acid-dye complex can be visualized with a UV transilluminator), 4) at least as sensitive as ethidium bromide (ease of use), 5) non-genotoxic (non-mutagenic and non-toxic) and 6) non-hazardous to aquatic life thus requiring no special waste disposal.

Here in we report the use of a class of unsymmetrical cyanine dye compounds (U.S. Pat. Nos. 4,883,867 and 4,957,870) for detecting immobilized nucleic acid polymers that is at least as sensitive as ethidium bromide, requires no additional reagents or instruments than ethidium bromide and can be made in large quantities. We also report on a compound in this class of dye compounds that is non-genotoxic and therefore requires no special handling or waste disposal procedures by the end user. Thus, this present invention is an improvement over currently used nucleic acid detection reagents and solves a problem not previously solved.

SUMMARY OF THE INVENTION

The present invention provides methods for determining the presence of immobilized nucleic acid employing unsymmetrical cyanine dyes, a staining solution and select fluorogenic compounds that are characterized as being essentially non-genotoxic. The methods comprise immobilizing nucleic acid, single or double stranded DNA, RNA or a combination thereof, on a solid or semi solid support, contacting the immobilized nucleic acid with an unsymmetrical cyanine dye compound and then illuminating the immobilized nucleic acid with an appropriate wavelength whereby the presence of the nucleic acid is determined. The cyanine dye compounds are typically present in an aqueous staining solution comprising the dye compound and a tris acetate or tris borate buffer wherein the solution facilitates the contact of the dye compound and the immobilized nucleic acid. Typically the solid or semi-solid support is selected from the group consisting of a polymeric gel, a membrane, an array, a glass, and a polymeric microparticle. Preferably, the polymeric gel is agarose or polyacrylamide.

Alternatively, the invention provides methods wherein the nucleic acid is contacted with the cyanine dye compounds to pre-stain the nucleic acid and then immobilized on a solid or semi-solid support. When this method is used with a polymeric gel such as agarose or polyacrylamide gel the nucleic acid is pre-stained and then immobilized on the gel, typically by electrophoresis. However, the pre-stained nucleic acid may also be immobilized on other supports such as a glass slide or polymeric beads. In another aspect, when polymeric gels are employed the cyanine dye compounds can be mixed with unpolymerized gel and then solidified. In this method, the nucleic acid is immobilized in the gel and detected wherein the cyanine dye binds the nucleic acid producing a fluorescent detectable signal. The cyanine dye compounds of the present methods are fluorogenic, they have a low intrinsic fluorescence when not associated with nucleic acid, but when bound to or associated with nucleic acid become fluorescent. This is an improvement over ethidium bromide wherein the compound has significant intrinsic fluorescence and displays a 20-25-fold increase in fluorescence upon intercalating into double stranded regions of nucleic acid (J. B. LePecq Anal. Biochem. 17 (1966) 100-107).

The cyanine dye compounds of the present invention include any compound disclosed in U.S. Pat. Nos. 4,883,867 and 4,957,870, supra. These cyanine dye compounds have the following formula

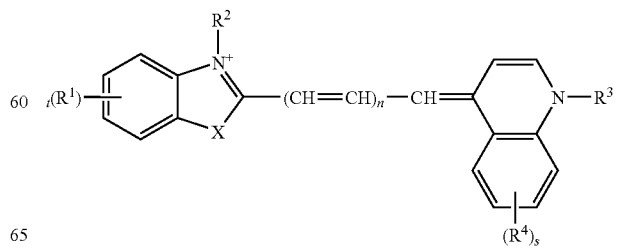

wherein X is O, S or C(CH$_3$)$_2$, R$^1$ is a fused benzene, C$_1$-C$_6$ alkoxy, or a C$_1$-C$_6$ alkyl, R$^2$ and R$^3$ are independently a C$_1$-C$_6$ alkyl and R$^4$ is a C$_1$-C$_6$ alkyl or a C$_1$-C$_6$ alkoxy, wherein t is independently 0, 1, 2, 3, or 4 and s is independently 0, 1, 2, 3, or 4. n is 0, 1, 2 or 3, with the proviso that the dye is not thiazole orange when used to detect DNA in a gel.

These cyanine dye compounds have previously been disclosed for use in detecting reticulocytes in a blood sample but herein we report a novel use for these compounds as fluorogenic dyes for immobilized nucleic acid polymers. In a preferred embodiment the cyanine dye compounds are employed as gel stains for nucleic acid polymers separated by electrophoresis, preferably DNA.

We have unexpectedly found that certain select unsymmetrical cyanine dye compounds can be characterized as being essentially non-genotoxic. The most widely used DNA gel stain is ethidium bromide, however this compound is a known mutagen and thus requires special handling and waste disposal. We herein report on an unsymmetrical cyanine dye compound that is at least as sensitive as ethidium bromide and based on an Ames test, in vitro transformation test, forward mutation screen and a screen for chromosomal aberrations is essentially non-mutagenic and non-toxic (Examples 2-5). Therefore, identification of an essentially non-genotoxic dye compound that is at least as sensitive as ethidium bromide overcomes the limitations of ethidium bromide by solving the problem of special handling and waste disposal not previously solved (See, Example 7). In addition, the dye compounds are excited by UV light, are easy to use and synthesize in large quantities. The identification of non-genotoxic compounds provides a DNA gel stain that does not poses a mutagenic or toxic hazard to the end user. This was an unexpected finding because compounds that bind or associate with nucleic acid are considered as potential mutagens by possibly interfering with replication.

For comparison purposes the compounds thiazole orange, ethidium bromide and a compound having the formula Compound 1

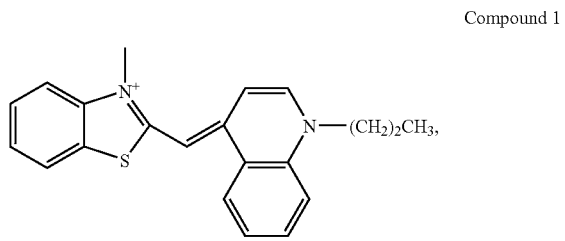

were tested for their ability to induce genetic mutations and toxicity levels in cells. The tests demonstrated that Compound 1, a thiazole orange derivative, is characterized as being essentially non-genotoxic while thiazole orange can not be characterized as such based on the tests performed. Therefore, this compound is preferred for the detection of immobilized nucleic acid wherein the compound posses no genotoxic (mutagenic or toxic) hazard to the end user.

Thus, the present invention provides improved methods for the detection of immobilized nucleic acid employing thiazole orange derivative cyanine dye compounds of the present invention and an aqueous staining solution. A particularly preferred improvement is the use of Compound 1 for the detection of immobilized nucleic acid.

DETAILED DESCRIPTION OF THE INVENTION

Definitions

Figure 1A:
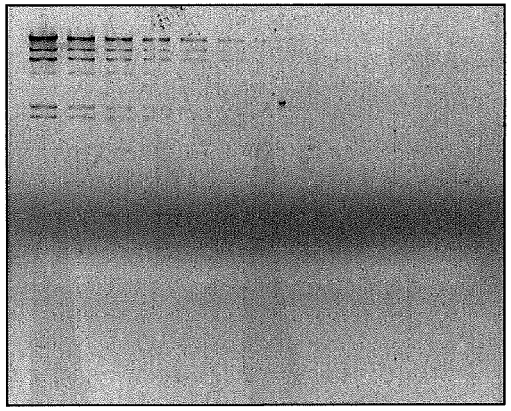
FIG. 1: Shows the detection of DNA, pre- (FIGS. 1A and D) and post-stained (FIGS. 1C and B), in an agarose gel using thiazole orange (FIGS. 1A and B) and Compound 1 (FIGS. 1C and D). See, Example 1
FIG. 1C is post stained for 60 minutes and FIG. 1D for 90 minutes. See, Example 6.
Figure 1B:
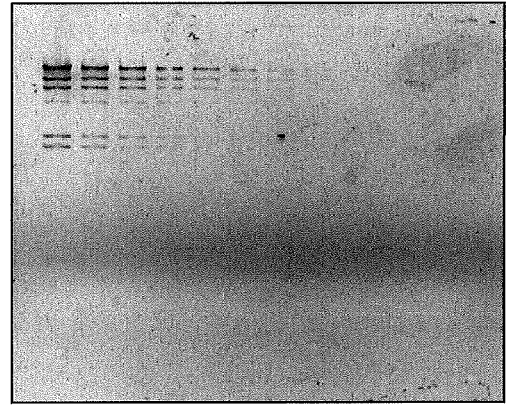
Figure 1C:
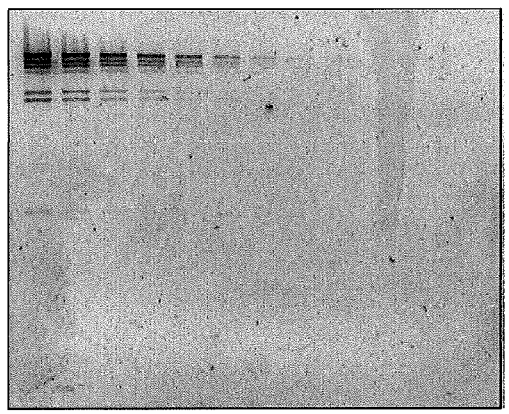
Figure 1D:
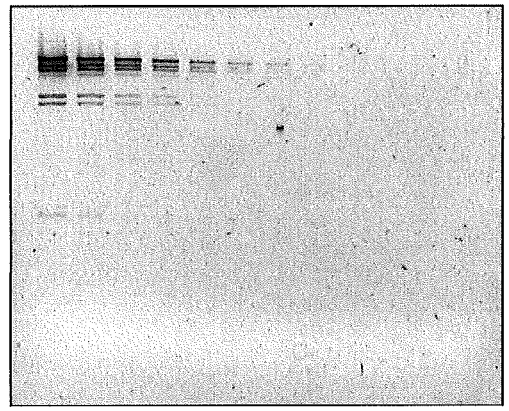

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a cyanine dye compound" includes a plurality of compounds and reference to "nucleic acid" includes a plurality of nucleic acids and the like.

Unless defined otherwise, all technical and scientific terms used herein have the same meaning as commonly understood by one of ordinary skill in the art to which this invention is related. The following terms are defined for purposes of the invention as described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.) VOGEL'S ENCYCLOPEDIA OF PRAC- TICAL ORGANIC CHEMISTRY 5$^{TH}$ ED., Longman Scientific and Technical Ltd., Essex, 1991, pp. 809-816; and Heller, *Acc. Chem. Res.* 23: 128 (1990).

Although typically not shown for the sake of clarity, any overall positive or negative charges possessed by any of the compounds of the invention are balanced by a necessary counterion or counterions. Where the compound of the invention is positively charged, the counterion is typically selected from, but not limited to, chloride, bromide, iodide, sulfate, alkanesulfonate, arylsulfonate, phosphate, perchlorate, tetrafluoroborate, tetraarylborate, nitrate, hexafluorophosphate, and anions of aromatic or aliphatic carboxylic acids. Where the compound of the invention is negatively charged, the counterion is typically selected from, but not limited to, alkali metal ions, alkaline earth metal ions, transition metal ions, ammonium or substituted ammonium ions. Preferably, any necessary counterion is biologically compatible, is not toxic as used, and does not have a substantially deleterious effect on biomolecules. Counterions are readily changed by methods well known in the art, such as ion-exchange chromatography, or selective precipitation.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty-five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P and S, and wherein the nitrogen, phosphorous and sulfur atoms are optionally oxidized, and the nitrogen heteroatom is optionally be quaternized, and the sulfur atoms are optionally trivalent with alkyl or heteroalkyl substituents. The heteroatom(s) O, N, P, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 4 rings), which are fused together or linked covalently. Specific examples of aryl substituents include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Preferred aryl substituents are phenyl, substituted phenyl, naphthyl or substituted naphthyl.

The term "heteroaryl" as used herein refers to an aryl group as defined above in which one or more carbon atoms have been replaced by a non-carbon atom, especially nitrogen, oxygen, or sulfur. For example, but not as a limitation, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridaziyl, triazinyl, piperidinyl, morpholinyl, thiomorpholinyl, pyrazinyl, piperainyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridinyl, phenazinyl, phenothizinyl, phenoxazinyl, purinyl, benzimidazolyl and benzthiazolyl and their aromatic ring-fused analogs. Many fluorophores are comprised of heteroaryl groups and include, without limitations, xanthenes, oxazines, benzazolium derivatives (including cyanines and carbocyanines), borapolyazaindacenes, benzofurans, indoles and quinazolones.

Where a ring substituent is a heteroaryl substituent, it is defined as a 5- or 6-membered heteroaromatic ring that is optionally fused to an additional six-membered aromatic ring(s), or is fused to one 5- or 6-membered heteroaromatic ring. The heteroaromatic rings contain at least 1 and as many as 3 heteroatoms that are selected from the group consisting of O, N or S in any combination. The heteroaryl substituent is bound by a single bond, and is optionally substituted as defined below.

Specific examples of heteroaryl moieties include, but are not limited to, substituted or unsubstituted derivatives of 2- or 3-furanyl; 2- or 3-thienyl; N-, 2- or 3-pyrrolyl; 2- or 3-benzofuranyl; 2- or 3-benzothienyl; N-, 2- or 3-indolyl; 2-, 3- or 4-pyridyl; 2-, 3- or 4-quinolyl; 1-, 3-, or 4-isoquinolyl; 2-, 4-, or 5-(1,3-oxazolyl); 2-benzoxazolyl; 2-, 4-, or 5-(1,3-thiazolyl); 2-benzothiazolyl; 3-, 4-, or 5-isoxazolyl; N-, 2-, or 4-imidazolyl; N-, or 2-benzimidazolyl; 1- or 2-naphthofuranyl; 1- or 2-naphthothienyl; N—, 2- or 3-benzindolyl; 2-, 3-, or 4-benzoquinolyl; 1-, 2-, 3-, or 4-acridinyl. Preferred heteroaryl substituents include substituted or unsubstituted 4-pyridyl, 2-thienyl, 2-pyrrolyl, 2-indolyl, 2-oxazolyl, 2-benzothiazolyl or 2-benzoxazolyl.

The above heterocyclic groups may further include one or more substituents at one or more carbon and/or non-carbon atoms of the heteroaryl group, e.g., alkyl; aryl; heterocycle; halogen; nitro; cyano; hydroxyl, alkoxyl or aryloxyl; thio or mercapto, alkyl- or arylthio; amino, alkyl-, aryl-, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or arylsulfonyl; hydroximinyl, or aryl- or alkoximinyl. In addition, two or more alkyl substituents may be combined to form fused heterocycle-alkyl ring systems. Substituents including heterocyclic groups (e.g., heteroaryloxy, and heteroaralkylthio) are defined by analogy to the above-described terms.

The term "heterocycloalkyl" as used herein refers to a heterocycle group that is joined to a parent structure by one or more alkyl groups as described above, e.g., 2-piperidylmethyl, and the like. The term "heterocycloalkyl" refers to a heteroaryl group that is joined to a parent structure by one or more alkyl groups as described above, e.g., 2-thienylmethyl, and the like.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R'''' groups when more than one of these groups is present. In the schemes that follow, the symbol X represents "R" as described above.

The aryl and heteroaryl substituents described herein are unsubstituted or optionally and independently substituted by H, halogen, cyano, sulfonic acid, carboxylic acid, nitro, alkyl, perfluoroalkyl, alkoxy, alkylthio, amino, monoalkylamino, dialkylamino or alkylamido.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "affinity" as used herein refers to the strength of the binding interaction of two molecules, such as an antibody and a ligand or antigen or a positively charged moiety and a negatively charged moiety. For bivalent molecules such as antibodies, affinity is typically defined as the binding strength of one binding domain for the antigen, e.g. one Fab fragment for the antigen. The binding strength of both binding domains together for the antigen is referred to as "avidity". As used herein "High affinity" refers to a ligand that binds to an antibody having an affinity constant (K$_a$) greater than 10$^4$ M$^{-1}$, typically 10$^5$-10$^{11}$ M$^{-1}$; m as determined by inhibition ELISA or an equivalent affinity determined by comparable techniques such as, for example, Scatchard plots or using K$_d$/dissociation constant, which is the reciprocal of the K$_a$, etc.

The term "aqueous solution" as used herein refers to a solution that is predominantly water and retains the solution characteristics of water. Where the aqueous solution contains solvents in addition to water, water is typically the predominant solvent.

The term "complex" as used herein refers to the association of two or more molecules, usually by non-covalent bonding.

The term "cyanine monomer" or "cyanine dye" as used herein refers to a fluorogenic compound that comprises 1) a substituted benzazolium moiety, 2) a polymethine bridge and 3) a substituted or unsubstituted pyridinium or quinolinium moiety. These monomer or dye moieties are capable of forming a non-covalent complex with nucleic acid and demonstrating an increased fluorescent signal after formation of the nucleic acid-dye complex.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "essentially non-genotoxic" as used herein refers to a substance that causes an insignificant amount of toxicity or mutations to a prokaryotic and/or eukaryotic cell when in contact with the cells. The non-genotoxic effect of a substance is determined by tests and screening assays well known in the art including, but not limited to, an Ames test, chromosomal aberration test, forward mutation screen and a test that determines LC$_{50}$ values.

The term "genotoxic" as used herein refers to a substance that causes toxicity and/or mutations to the prokaryotic and or eukaryotic cells resulting in abnormal cell growth including death and uncontrolled growth of the cell or organism.

The term "kit" as used refers to a packaged set of related components, typically one or more compounds or compositions.

The term "mutagenic" as used herein refers to a substance that causes mutations to the nucleic acid of a cell or organism including point mutations, frameshift mutations and deletion mutations.

The term "nucleic acid polymer" as used herein refers to natural or synthetic polymers of DNA or RNA that are single, double, triple or quadruple stranded. Polymers are two or more bases in length. The term "nucleic acid" is herein used interchangeably with "nucleic acid polymer".

The term "sample" as used herein refers to any material that may contain a target nucleic acid. Typically, the sample is immobilized on a solid or semi solid surface such as a polyacrylamide gel, membrane blot or on a microarray that contains nucleic acid polymers, nucleotides, oligonucleotides, but may be in an aqueous solution or a viable cell culture. However, the sample may be a live cell, a biological fluid that comprises endogenous host cell proteins, peptides and buffer solutions.

Compound and Compositions

The present invention provides improved methods for determining the presence of immobilized nucleic acid, an aqueous staining solution and nucleic acid complexing compounds. In one aspect of the invention, the improvement consists of the use of cyanine dye compounds that are characterized as being essentially non-genotoxic. These compounds are an improvement over currently used nucleic acid detection agents that are generally considered to be toxic and/or mutagenic and poses a health risk to the end user and environment wherein precautionary measures need to be followed to ensure there is no direct contact between the nucleic acid detection reagent, such as ethidium bromide, and the user. Thus, the discovery of a non-genotoxic nucleic acid detection agent is an important improvement that is safe to handle for the end user and can be disposed of as non-hazardous waste, i.e. safe to the environment (Example 7). Herein we report an improved method for the detection of nucleic acid that does not require special handling or waste disposal but retains all of the advantages of commonly used ethidium bromide.

A number of different classes of compounds were tested that are known or thought to associate with immobilized DNA. Typically, the nucleic acid complexing compound are unsymmetrical cyanine dyes including, but are not limited to, dyes sold under the trade name SYBR® dyes (Molecular Probes, Inc.), thiazole orange, their derivatives and any monomer compound disclosed in U.S. Pat. Nos. 4,957,870; 4,883,867; 5,436,134; 5,658,751; 5,534,416 and 5,863,753. These compounds were simultaneously screened in an Ames test for their ability to induce mutations in *Salmonella typh*-

*imurium* wherein the goal was to develop an improved method for the detection of immobilized nucleic acid such that the dye compound employed was at least, or more, sensitive than ethidium bromide but with reduced genotoxic effects compared to ethidium bromide. The results of these early screens indicated that two compounds, thiazole orange and Compound 1, were either mildly mutagenic or non-mutagenic and that both were able to detect nucleic acid that had been immobilized in a gel by electrophoresis when excited with UV light, about 300 nm, See Example 1. For comparison purposes ethidium bromide was tested with Thiazole orange and Compound 1 along with the appropriate controls, See Example 2-5.

Thus, in one aspect of the invention, compounds disclosed in U.S. Pat. Nos. 4,883,867 and 4,957,870 (supra) are preferred for use in determining the presence of immobilized nucleic acid. These cyanine dye compounds have the following formula

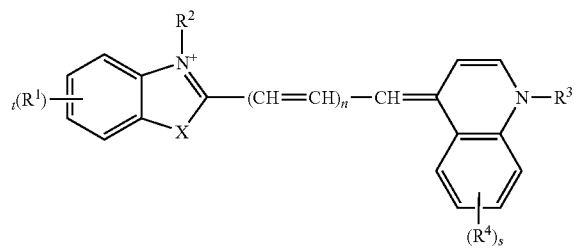

a)

wherein X is O, S or $C(CH_3)_2$, $R^1$ is a fused benzene, $C_1$-$C_6$ alkoxy, or a $C_1$-$C_6$ alkyl, $R^2$ and $R^3$ are independently a $C_1$-$C_6$ alkyl and $R^4$ is a $C_1$-$C_6$ alkyl or a $C_1$-$C_6$ alkoxy, wherein t is independently 0, 1, 2, 3, or 4 and s is independently 0, 1, 2, 3 or 4. n is 0, 1, 2 or 3.

In a preferred embodiment the dye compound is either thiazole orange

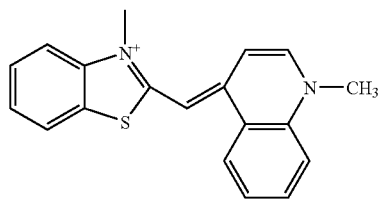

or Compound 1 having the formula:

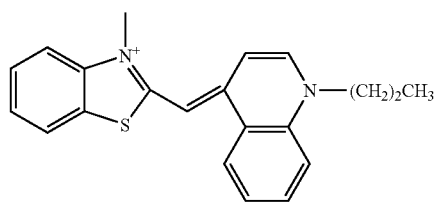

wherein $R^1$ is hydrogen, $R^2$ is methyl, n is 0, $R^4$ is hydrogen and $R^3$ is either methyl (thiazole orange) or propyl (Compound 1). However, the use of thiazole orange for detection of DNA in a gel is not an aspect of the present invention (Rye et al. Nucleic Acids Res. 19(2) (1991) 327-33). Therefore, Compound 1 is preferred for the detection of nucleic acid that has been immobilized on a polymeric gel.

These dyes have a low intrinsic fluorescence but upon binding to nucleic acid demonstrate significant increase in fluorescence. These dye compounds have a maxima excitation between 480 and 520 nm, however these compounds may be excited by UV light, which is typically understood to be below 400 nm. Thus, the cyanine dye compounds can be excited using a UV transilluminator, as is typically used for ethidium bromide stained gels containing separated nucleic acid. The excitation of these dyes is typically in the range of about 530 to 600 nm. Ethidium bromide can be excited by UV light but has an optima absorption of 540 nm, when associated with DNA, and an emission of 620 nm. Thus, the present cyanine dye compounds, including Compound 1, fit the criteria of being excitable by UV light and possessing similar excitation emission compared to ethidium bromide.

Thiazole orange and Compound 1 were tested in an Ames test and compared to previously tested ethidium bromide (Singer et al. (1999) supra) (Example 2). All three compounds, ethidium bromide, Thiazole orange and Compound 1, were tested in an in vitro transformation test (Example 3), forward mutation screen (Example 4) and a screen for chromosomal aberrations (Example 5). This panel of tests results in the identification of compounds that are either genotoxic or non-genotoxic wherein genotoxic is defined to include both cell cytoxicity effects and genetic mutations. It is appreciated by one skilled in the art that these tests can be used to screen other compounds for their genotoxic effects that are to be used to detect immobilized nucleic acid polymers. Unexpectedly, based on these tests, thiazole orange is considered genotoxic but the thiazole analog Compound 1 is characterized as being essentially non-genotoxic. In addition, Compound 1 was tested to determine if the compound is hazardous or toxic to aquatic life wherein Compound 1 has an $LC_{50}$ value >500 mg/L and is characterized as being non-hazardous to aquatic life (Example 7).

Based on the tests performed, Compound 1 does not cause mutations in mouse lymphoma cells at the thymidine kinase (TK) locus, nor does it induce chromosomal aberrations in cultured human peripheral blood lymphocytes, with or without S9 metabolic activation. In addition, Compound 1 did not transform Syrian hamster embryo (SHE) cell cultures. This latter test has a high concordance (>80%) with rodent carcinogenesis, so a negative test strongly indicates that Compound 1 is noncarcinogenic. Thus, Compound 1 is not a dangerous laboratory reagent by three independent assessments of potential genotoxicity to mammalian cells. In contrast, ethidium bromide tests positive in the SHE assay, indicating that this stain will be found carcinogenic to rodents. Two-year bioassay studies for ethidium bromide have not yet been reported.

TABLE 1

| Test* | Ethidium bromide | Compound 1 | Thiazole orange |
|---|---|---|---|
| Transformation Test [1] Syrian hamster embryo (SHE) cells | positive | negative | positive |
| Chromosomal Aberrations Test [2] Cultured human peripheral blood lymphocytes | negative | negative | negative |

TABLE 1-continued

| Test* | Ethidium bromide | Compound 1 | Thiazole orange |
|---|---|---|---|
| Forward Mutation Test [3] L5178YTK<sup>+/−</sup> mouse lymphoma cells | negative | negative | negative |

[1] Yamasaki (1996) Fundamental and Molecular Mechanisms of Mutagenesis Special Issue 356 1-128;
[2] Evans (1976) Cytological Methods for Detecting Chemical Mutagens in Chemical Mutagens, Principles and Methods for their Detection, Hollaender (ed). Vol. 4: 1-29;
[3] Amacher et al (1980) Mutation Research 72: 447-474; Clive et al (1979) Mutation Research 59: 61-108.

Compound 1 causes fewer mutations in the Ames test, compared to ethidium bromide and thiazole orange, as measured in several different strains of *Salmonella typhimurium*, See FIG. 1 and Table 2. Weakly positive results (Compound 1) in this test occurred in three out of seven strains and only after activation by a mammalian S9 fraction obtained from rat liver, as shown in FIG. 1.

Methods of Use

The staining solution can be prepared in a variety of ways, which are dependent on the method and the medium in which the sample is present, as described below. Specifically the staining solution comprises a present unsymmetrical cyanine dye and buffering components that are compatible with nucleic acid, optionally the staining solution comprises an organic solvent or a mixture of organic solvents and additional ionic or nonionic components. Any of the components of the staining solution can be added together or separately and in no particular order and, as will become evident, the cyanine dye compound may be immobilized on a solid or semi-solid matrix, wherein the buffering components are added to the matrix to form the staining solution of the present invention. Therefore, the cyanine compounds do not need to free in the staining solution to form the solution but may be immobilized on a solid or semi-solid matrix surface. Alternatively the cyanine compounds are immobilized on or in a solid or semi-solid matrix wherein the dye compound is transferred to the immobilized nucleic acid in the absence of a buffer. In another aspect the cyanine dye compound is immobilized in a polymeric gel that is a buffer-less system such as E-gels (Invitrogen Corp).

The staining solution is typically prepared by dissolving a present unsymmetrical cyanine dye compound in an aqueous solvent such as water, a buffer solution, such as phosphate buffered saline, or an organic solvent such as dimethylsulfoxide (DMSO), dimethylformamide (DMF), methanol, ethanol or acetonitrile. Typically, the present cyanine dye compounds are first dissolved in an organic solvent such as DMSO as a stock solution. Typically the stock solution is about 100-fold to about 10,000-fold concentrated compared to the working concentration.

In one aspect, the stock solution is then diluted to an effective working concentration in an aqueous solution optionally comprising appropriate buffering components to form a buffer solution comprising a dye compound of the present invention and a trace amount of the organic solvent. The buffer solution is typically phosphate buffered saline (PBS), tris acetate (TAE) or tris borate (TBE). Preferably the staining solution comprises a cyanine dye of the present invention, TAE or TBE and a trace amount of DMSO. An effective working concentration of the present compounds is the amount sufficient to give a detectable fluorescent response when complexed with nucleic acid polymers. Typically, the effective amount is about 100 nm to 100 μM. Preferred is about 600 nm to 10 μM and most preferred is about 1 μM. It is generally understood that the specific amount of the dye compound present in a staining solution is determined by the physical nature of the sample and the nature of the analysis being performed.

An aqueous staining solution of the present invention for determining the presence of immobilized nucleic acid on a solid or semi-solid support wherein the nucleic acid is essentially free of intact cells or cellular organelles, comprises an unsymmetrical cyanine dye compound of the present invention, a tris borate or tris acetate buffer and a trace amount of organic solvent that was used to solubilize the dye compound. The staining solution typically has a pH of about 6 to about 8 and the solid or semi-solid support is selected from the group consisting of a polymeric gel, a membrane, an array, a glass, and a polymeric microparticle. In one aspect of the invention, the solution optionally further comprises unpolymerized agarose or polyacrylamide such that the dye compound forms part of the gel and the nucleic acid sample comes in contact with the dye compound when immobilized on the gel.

Thus, the dye stock solution is diluted and mixed with agarose and/or agarose and buffer, wherein the nucleic acid is immobilized in the agarose that contains a present compound. The agarose may be in the form of a tablet, pre-cast gel or solidified agarose that is ready to be heated and poured into a slab gel. One possible form of this would be a mixture of agarose/TBE/and a present compound at the concentrations that would be used for electrophoretic separation of nucleic acids. Heating the mixture until molten, mixing, and allowing to cool to room temperature. At anytime in the future the solid mixture may be reheated and poured for use without the need for measuring of components or mixing prior to use. Another iteration of this concept would be to blend the solid form of the dye with solid powdered agarose (which can either be stored as a powder or compressed into tablets) and stored. When needed the powder may be weighed and added to buffer for use without the need to separately measure and add the dye.

In yet another aspect, the present compounds are impregnated in a polymeric membrane, such as InstStain papers (Edvotek), wherein the membrane is contacted with the immobilized nucleic acid resulting in a transfer of the dye from the membrane to the nucleic acid.

In one aspect of the invention, a method for determining the presence or absence of nucleic acid immobilized on a solid or semi solid support comprises
  a) combining an unsymmetrical cyanine dye compound of the present invention with a sample to prepare a labeling mixture, wherein the sample is immobilized on a solid or semi-solid support;
  b) incubating the labeling mixture for a sufficient amount of time for the dye to associate with the nucleic acid to prepare an incubated sample;
  c) illuminating the incubated sample with an appropriate wavelength to prepare an illuminated sample; and
  d) observing the illuminated sample whereby the presence or absence of the nucleic acid is determined.

In one aspect of the invention, the nucleic acids in the sample mixture are separated from each other or from other ingredients in the sample by mobility (e.g. electrophoretic gel or capillary) or by size (e.g. centrifugation, pelleting or density gradient), or by binding affinity (e.g. to a filter membrane) in the course of the method. The sample is combined with the staining solution by any means that facilitates contact between the dye and the analyte. Thus, the present compounds may be staining solution, dried on a polymeric membrane or pre-mixed with the solid or semi-solid support that the nucleic acid is immobilized on. Typically the contact occurs through simple mixing, as in the case where the sample is a solution. A staining solution containing the dye may be added to the analyte solution directly or may contact the analyte solution in a liquid separation medium such as an electrophoretic liquid, sieving matrix or running buffer, or in a sedimentation (e.g. sucrose) or buoyant density gradient (e.g. containing CsCl), or on an inert matrix, such as a blot or gel, a testing strip, or any other solid or semi-solid support. Suitable supports also include, but are not limited to, polymeric microparticles (including paramagnetic microparticles), polyacrylamide and agarose gels, nitrocellulose filters, computer chips (such as silicon chips), natural and synthetic membranes, and glass (including optical filters), and other silica-based and plastic support. The dye is optionally combined with the analyte solution prior to undergoing gel or capillary electrophoresis, gradient centrifugation, or other separation step, during separation, or after the nucleic acids undergo separation. Alternatively, the dye is combined with an inert matrix or solution in a capillary prior to addition of the analyte solution, as in pre-cast gels, capillary electrophoresis or preformed density or sedimentation gradients.

The sample is incubated in the presence of the dye compounds for a time sufficient to form the fluorescent nucleic acid-dye compound complex. Detectable fluorescence in a solution of nucleic acids is essentially instantaneous. In general, visibly detectable fluorescence can be obtained in a wide variety of solid or semi-solid matrix with embodiments of the present invention within about 10-90 minutes after combination with the sample, commonly within about 20-60 minutes, most preferably about 30 minutes (See, Example 6). In this instance, a nucleic acid sample is immobilized on a polymeric gel, typically by electrophoresis, and then the gel is immersed in the staining solution wherein a detectable signal represents the presence of nucleic acid. It is readily apparent to one skilled in the art that the time necessary for sufficient formation of the fluorescent nucleic acid complex is dependent upon the physical and chemical nature of the individual sample and the sample medium.

In an alternative embodiment, the immobilized nucleic acid is overlaid with a membrane that contains a present cyanine dye compound. The compound transfers to the nucleic acid in a few minutes, typically less than about 10 minutes, to provided a labeled sample mixture.

To facilitate the detection of the nucleic acid-dye compound complex, the excitation or emission properties of the fluorescent complex are utilized. For example, the sample is excited or illuminated by a light source capable of producing light at or near the wavelength of maximum absorption of the fluorescent complex, such as an ultraviolet or visible lamp, an arc lamp, a laser, or even sunlight. Preferably the fluorescent complex is excited at a wavelength equal to or greater than about 280 nm, more preferably equal to or greater than about 300 nm. The resulting emission is detected by means that include visible inspection, photographic film, or the use of current instrumentation such as fluorometers, quantum counters, plate readers, epifluorescence microscopes and flow cytometers or by means for amplifying the signal such as a photomultiplier. In one aspect a UV transilluminator is used to illuminate the nucleic acid-dye compound complex. In another aspect a visible light transilluminator, such as a Dark Reader (Clare Chemical Research, Inc., CO) is used to illuminate the nucleic acid-dye compound complex.

In one aspect of the invention a method for determining the presence of nucleic acid polymer immobilized on a gel comprises the following steps:

a) immobilizing the nucleic acid polymers on a polymeric gel;
b) contacting the gel with a staining solution, wherein the staining solution comprises;
  i) an unsymmetrical cyanine dye compound having formula

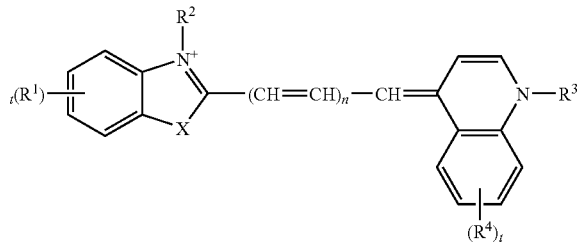

wherein X is O, S or $C(CH_3)_2$;
   $R^1$ is a fused benzene, methoxy, a $C_1$-$C_6$ alkyl;
   $R^2$ and $R^3$ are independently a $C_1$-$C_6$ alkyl;
   $R^4$ is a $C_1$-$C_6$ alkyl or a methoxy wherein t is independently 0, 1, 2, 3, or 4, and
   n is 0, 1, 2 or 3; and
  ii) a tris borate or tris acetate buffer,
c) incubating the gel of step b) and the staining solution for sufficient time to allow the cyanine dye compound to associate with the nucleic acid polymer; and,
d) illuminating the immobilized nucleic acid-cyanine dye complex with an appropriate wavelength whereby the presence of the nucleic acid is determined, with the provision that the cyanine dye compound is not thiazole orange.

Typically the gel is about a 3-0.5% agarose gel. Preferably the agarose gel is about a 1% gel. However, one of skill in the art will appreciate that the percentage of gel is somewhat dependent on the size of the nucleic acid polymers to be separated and immobilized.

The nucleic acid polymers are typically immobilized by electrophoresis wherein a current is applied to the agarose gel and the charged nucleic acid polymer migrate through the gel as a function of size. However, the nucleic acid polymers may be spotted onto the polymeric gel, typically agarose or polyacrylamide. In one aspect agarose E-gels (Invitrogen, CA) are used to separate and immobilize a sample containing nucleic acid.

In a preferred embodiment the cyanine dye compound is represented by Compound 1. In this instance, Compound 1 is characterized as being essentially non-genotoxic. Therefore, a preferred embodiment of the present invention is the improved method of determining the presence of nucleic acid using a compound that is essentially non-genotoxic. This method provides an improvement over currently used dye compounds to detect nucleic acid wherein compound 1 has not previously been disclosed to be non-genotoxic or disclosed for the use of detecting immobilized nucleic acid.

As described above, the gel is contacted with a present staining solution, typically by immersing the gel in the staining solution. The gel is typically immersed in the staining solution for about 10-90 minutes, preferably about 20-60 minutes, most preferred about 30 minutes. However, the running buffer, buffer used to conduct the current through the gel may be replaced by the staining solution of the present invention. In this instance, the nucleic acid is forming a complex with the cyanine dye while it is migrating through the gel. In this way, the step of incubating occurs simultaneously with the step of immobilizing and the step of contacting.

The stained agarose gel is typically illuminated with a UV transilluminator or a visible light transilluminator. However, any appropriate instrument that allows for visualization of the nucleic acid-dye complex, excites the fluorophore and records the excited wavelength generated by the fluorophore, may be used for the detection of the nucleic acid-dye complex.

In another aspect of the invention, the staining solution, comprising an unsymmetrical cyanine dye compound of the present invention, is combined with the unpolymerized gel such that the cyanine dye compound forms part of the solidified gel. In this instance, dry agarose is combined with buffer such as TBE and heated to dissolve the dry agarose. Prior to solidifying a stock solution of the cyanine dye compound is added to the liquefied agarose in buffer. Therefore, the steps of immobilizing, contacting and incubating occur simultaneously in this aspect of the invention.

Sample Preparation

The end user will determine the choice of the sample and the way in which the sample is prepared but the sample is typically prepared using methods well known in the art for isolating nucleic acid for in vitro solution based assay detection or well know methods for detection of nucleic acids that have been immobilized on a solid or semi-solid matrix. The sample includes, without limitation, any biological derived material that is thought to contain a nucleic acid polymer. Alternatively, samples also include material that nucleic acid polymers have been added to such as a PCR reaction mixture, a polymer gel such as agarose or polyacrylamide gels or a microfluidic assay system. In another aspect of the invention, the sample can also include a buffer solution that contains nucleic acid polymers to determine the present dye compounds that are ideal under different assay conditions or to determine the present dye compounds that are essentially non-genotoxic.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells such as bacteria, yeast, fungi, mycobacteria and mycoplasma, and eukaryotic cells such as nucleated plant and animal cells that include primary cultures and immortalized cell lines. Typically prokaryotic cells include *E. coli* and *S. aureus*. Eukaryotic cells include without limitation ovary cells, epithelial cells, circulating immune cells, β cells, hepatocytes, and neurons.

The nucleic acid may be either natural (biological in origin) or synthetic (prepared artificially). The nucleic acid may be present as nucleic acid fragments, oligonucleotides, or nucleic acid polymers. The nucleic acid may be present in a condensed phase, such as a chromosome. The presence of the nucleic acid in the sample may be due to a successful or unsuccessful experimental methodology, undesirable contamination, or a disease state. Nucleic acid may be present in all, or only part, of a sample, and the presence of nucleic acids may be used to distinguish between individual samples, or to differentiate a portion or region within a single sample.

The nucleic acid may be enclosed in a biological structure, for example contained within a viral particle, an organelle, or within a cell. The nucleic acids enclosed in biological structures may be obtained from a wide variety of environments, including cultured cells, organisms or tissues, unfiltered or separated biological fluids such as urine, cerebrospinal fluid, blood, lymph fluids, tissue homogenate, mucous, saliva, stool, or physiological secretions or environmental samples such as soil, water and air. The nucleic acid may be endogenous or introduced as foreign material, such as by infection or by transfection.

Alternatively, the nucleic acid is not enclosed within a biological structure, but is present as a sample solution. The sample solution can vary from one of purified nucleic acids to crude mixtures such as cell extracts, biological fluids and environmental samples. In some cases it is desirable to separate the nucleic acids from a mixture of biomolecules or fluids in the solution prior to combination with the present cyanine dye compounds. Numerous, well known, techniques exist for separation and purification of nucleic acids from generally crude mixtures with other proteins or other biological molecules. These include such means as electrophoretic techniques and chromatographic techniques using a variety of supports.

Illumination

The sample containing a nucleic acid-dye compound complex is illuminated with a wavelength of light selected to give a detectable optical response, and observed with a means for detecting the optical response. Equipment that is useful for illuminating the present compounds and compositions of the invention includes, but is not limited to, a UV transilluminator, hand-held ultraviolet lamps, mercury arc lamps, xenon lamps, lasers, laser diodes and a Dark Reader or any transilluminator disclosed in U.S. Pat. Nos. 6,512,236 and 6,198,107. These illumination sources are optically integrated into laser scanners, fuorescences microplate readers or standard or microfluorometers.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes.

The wavelengths of the excitation and emission bands of the nucleic acid dye compounds vary with dye compound composition to encompass a wide range of illumination and detection bands. This allows the selection of individual dye compounds for use with a specific excitation source or detection filter.

Kits

Suitable kits for forming a nucleic acid-dye compound complex and detecting the nucleic acid also form part of the invention. Such kits can be prepared from readily available materials and reagents and can come in a variety of embodiments. The contents of the kit will depend on the design of the assay protocol or reagent for detection or measurement. All kits will contain instructions, appropriate reagents, and present nucleic acid dye compounds. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above.

In one aspect of the invention, a kit contains a solution that comprises an organic solvent and an unsymmetrical cyanine dye compound of the present invention. Typically the solution further contains a buffering component wherein the buffering component is preferably tris acetate or tris borate. The organic solvent is typically an alcohol or DMSO. The kit may contain the staining solution as a concentrate or a 1× ready to use concentration.

Kits may further comprise InstaStain papers, such as those provided by Edvotek (Bethesda, Md.) including any article disclosed in EP1057001 and WO9942620, wherein the staining solution has been dried down on or impregnated into the papers. The paper is then applied to the gel wherein the dye in the InstaStain paper is transferred to the gel. The kits may further comprise polymerized agarose, either in the form of a precast gel, such as E-gels (Ethrog/Invitrogen, including any gel disclosed in U.S. Pat. Nos. 6,562,213; 5,865,974; 5,582,702; 6,379,516; Published U.S. Patent Application 20020134680 and US2002/0112960 and published PCT application WO 96/34276 and WO 97/41070), or in a form that needs to be liquefied and then poured into an appropriate gel slab, such as the Gel-O Shooters sold by Continental Laboratory Products (San Diego, Calif.) or the Heat and Pour Agarose sold by IPM Scientific (Eldersburg, Md.). In this instance, the staining solution may be premixed with the polymerized agarose, added during the liquid phase or added after polymerization. In another aspect the kit contains a tablet of agarose that needs to have buffer added and then poured into a slab, such as the agarose tablets sold by Bioline (Randolf, Mass.). The staining solution may be premixed in the tablet or provided in a separate vial to be added to the agarose at a step determined by the end user.

For a kit that is not hazardous to the end user, non-genotoxic, and is used to detect nucleic acid immobilized in a polymeric gel the staining solution in the kit typically contains the organic solvent DMSO, the buffer tris acetate or tris borate and compound 1.

A kit of the invention may optionally further comprise nucleic acid fragments to be used as size markers, controls, additional detection reagents such as dye compounds specific for only DNA or specific only for RNA.

A detailed description of the invention having been provided above, the following examples are given for the purpose of illustrating the invention and shall not be construed as being a limitation on the scope of the invention or claims.

EXAMPLES

Example 1

Detection of DNA in an Agarose Gel with Thiazole Orange and Compound 1

Different concentrations of DNA (62.5 ng, 31.25 ng, 15.63 ng, 7.813 ng, 3.906 ng, 1.953 ng, 976.6 pg, 488.3 pg, 244.1 pg, 122.1 pg, 61.04 pg and 30.52 pg) were loaded and separated on a 1% agarose gel at 80 v in 0.5×TBE. The gels were stained with a staining solution comprising TBE (50 mL) and either thiazole orange or compound 1 (4.54 µl of dye stock solution in DMSO). Alternatively, the gels were prepared to contain either thiazole orange or Compound 1 wherein 1 g of agarose, 100 ml of 0.5×TBE was mixed with either 9.08 µl of thiazole orange or Compound 1 stock solution. The DNA was loaded and separated in 0.5×TBE at 80 v. Some of these gels were also post stained with staining solution. All gels were subsequently photographed. These gels demonstrate the ability of thiazole orange and a derivative thereof to detect nucleic acid separated and immobilized in a gel. See, FIG. 1.

Example 2

*Salmonella*/Mammalian Microsomal Reverse Mutation Assay (Ames Test)

The Ames assay was performed using the method described by Ames (Ames et al Mutation Research 31 (1975) 347-364; Levin et al. PNAS 79 (1982) 7445-7449; Maron and Ames, Mutation Research 113 (1983) 173-215). Tester stains used were *Salmonella typhimurium* histidine auxotrophs TA97a, TA98, TA100, TA102, TA1535, TA1537 and TA1538. The assay was performed with test compounds (Ethidium bromide, thiazole orange and Compound 1) at six doses in both the presence and absence of S9 (rat liver extract), along with appropriate vehicle and positive controls (Singer et al. Mutation Research 439 (1999) 37-47). The test compounds, test vehicle and S9 (when appropriate) were combined with molten agar and then overlaid over a minimal agar plate. Following incubation at 37° C., revertant colonies were counted. When S9 was not used, 100 µl of tester strain and 50 µl of control or test compound were added to 2.5 ml of selective top agar. When S9 was used, 500 µl of S9 mix, 100 µl of tester strain and 50 µl of control or test compound was added to 2.0 ml of selective top agar. The top agar was then overlaid onto the surface of 25 ml of minimal bottom agar contained in a 15×100 mm Petri dish. The inverted plates were incubated for 52±4 hr at 37±2° C.

Figure 2:
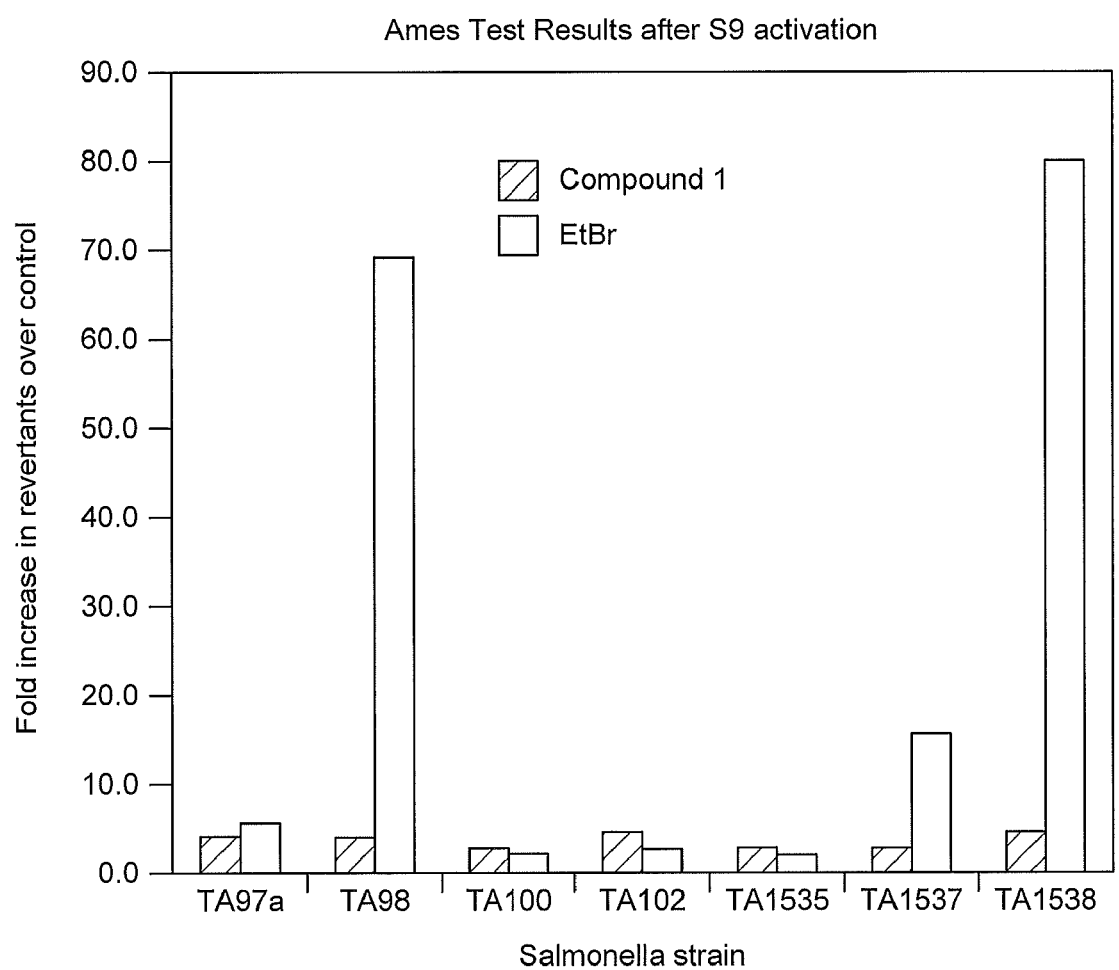
FIG. 2: Shows the comparison between ethidium bromide and Compound 1 in the Ames test. See, Example 2.
Figure 3A:
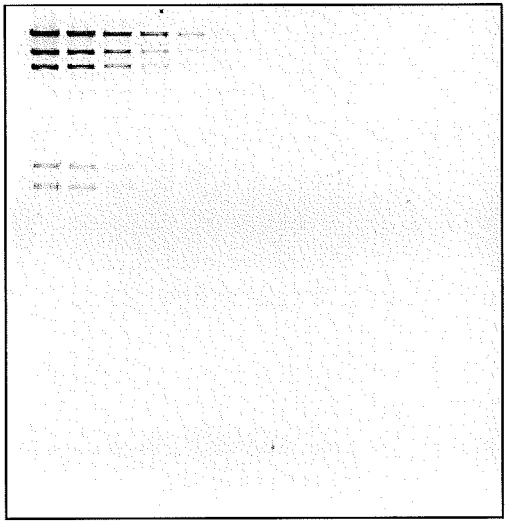
FIG. 3: shows a comparison between DNA stained with ethidium bromide (FIG. 1A) and Compound 1 (FIG. 1B-D) wherein FIGS. 1A and B are post stained for 30 minutes
Figure 3B:
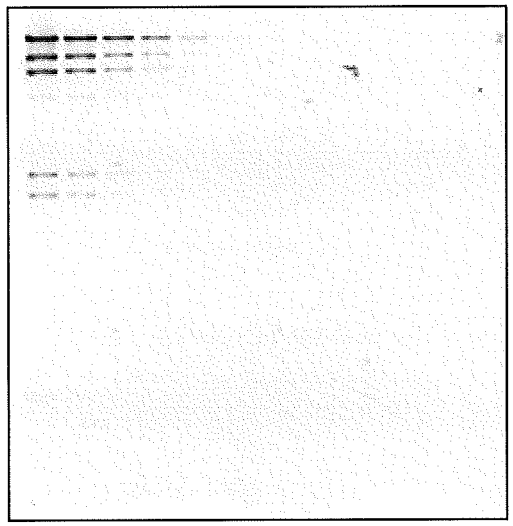
Figure 3C:
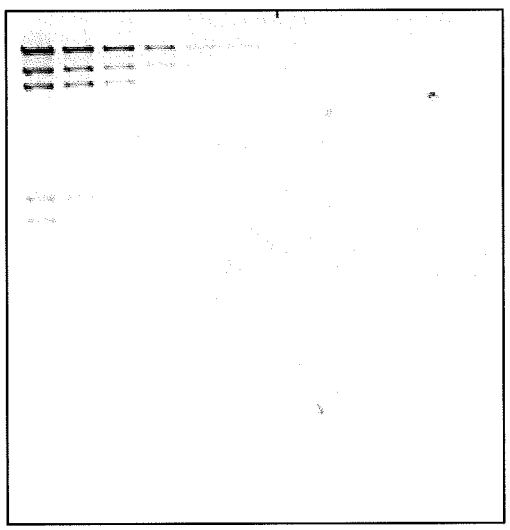
Figure 3D:
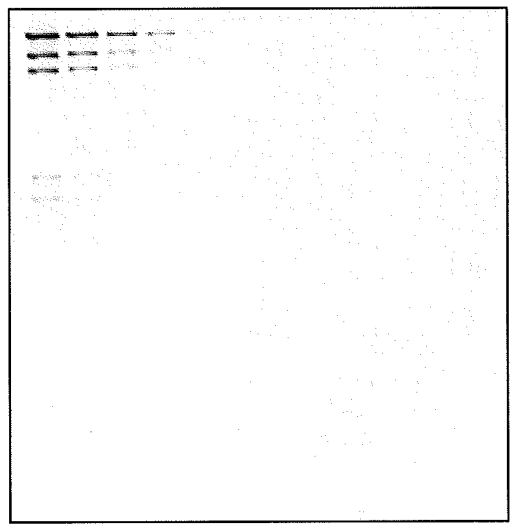
Figure 4A:
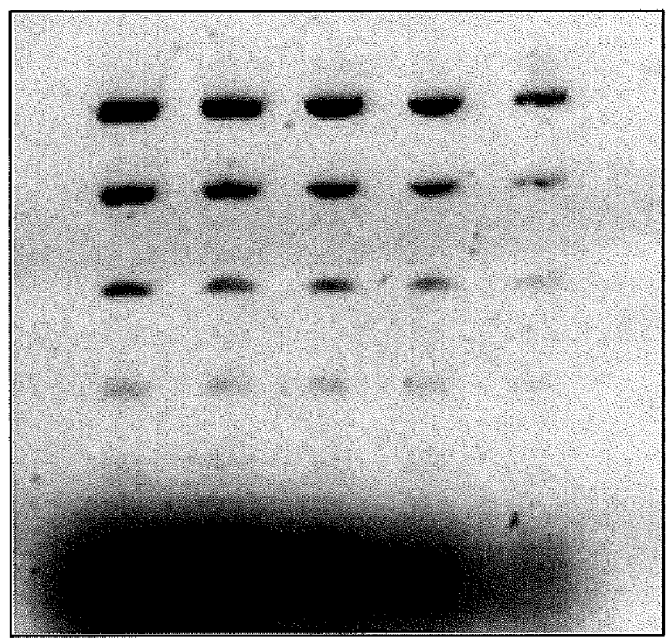
FIG. 4: Shows the detection of DNA on an E-gel visualized with a UV transilluminator and a Dark Reader (Clare Chemical Research). Different quantities of Low DNA Mass Ladder (1 µl, 0.5 µl, 0.25 µl, 0.13 µl), were loaded on an E-Gel (2%), where the ethidium bromide has been replaced by a 4× concentration of Compound 1. The gels were run for 30 minutes, then visualized with a transilluminator. See, Example 9.
Figure 4A:
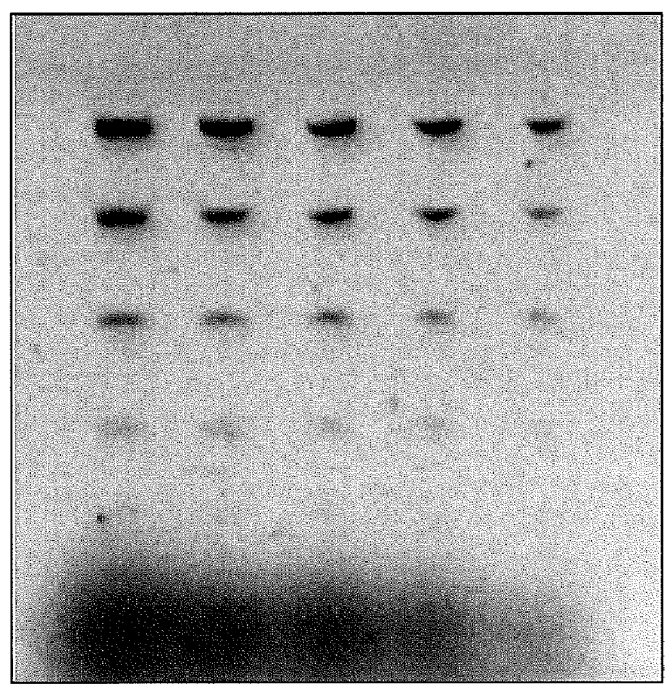
Figure 4B:
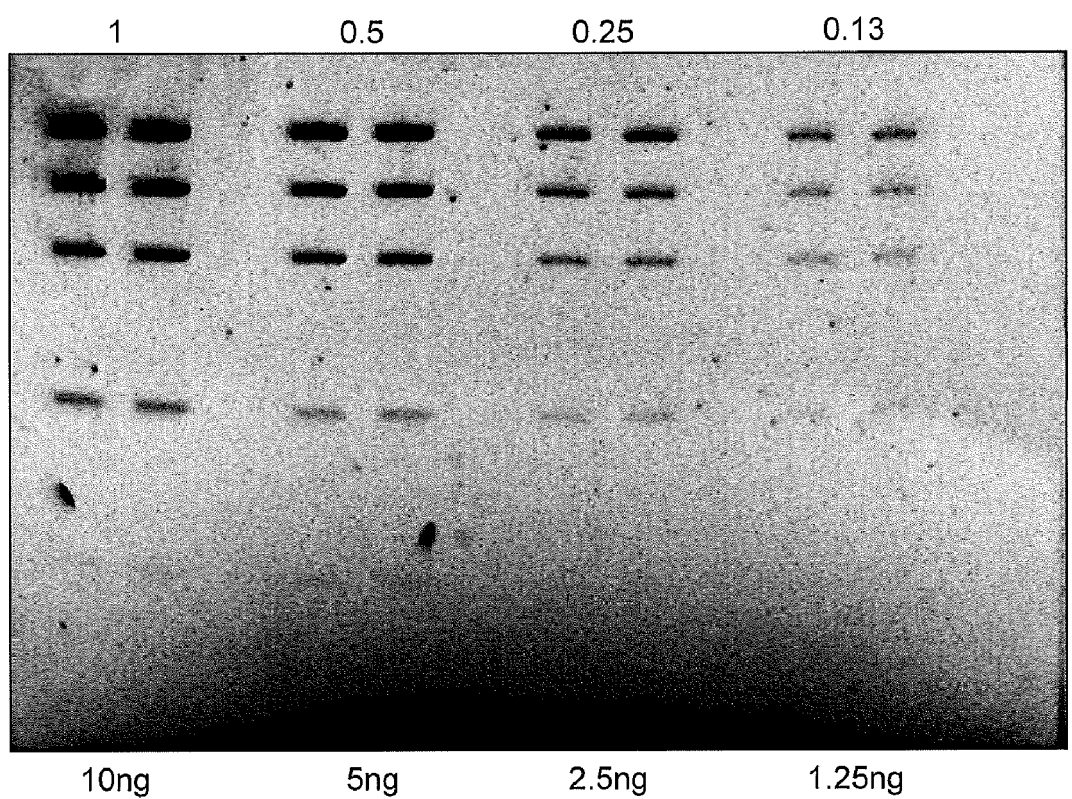
Figure 4C:
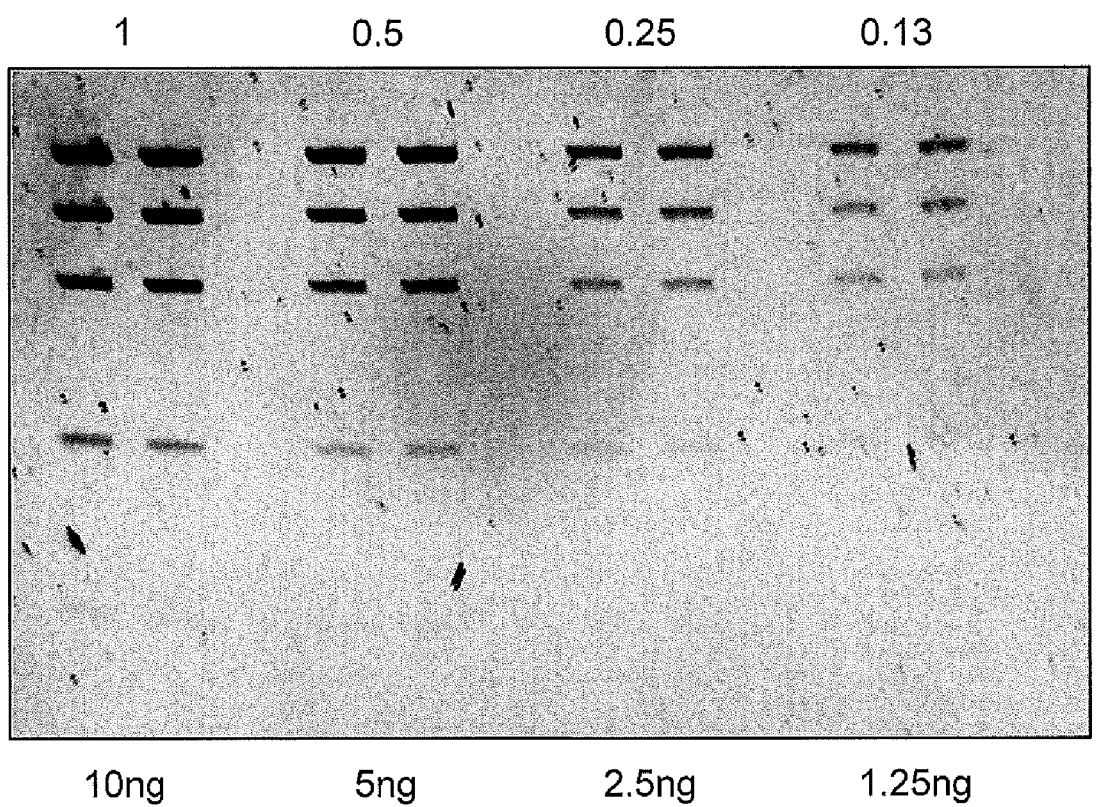
Figure 4D:
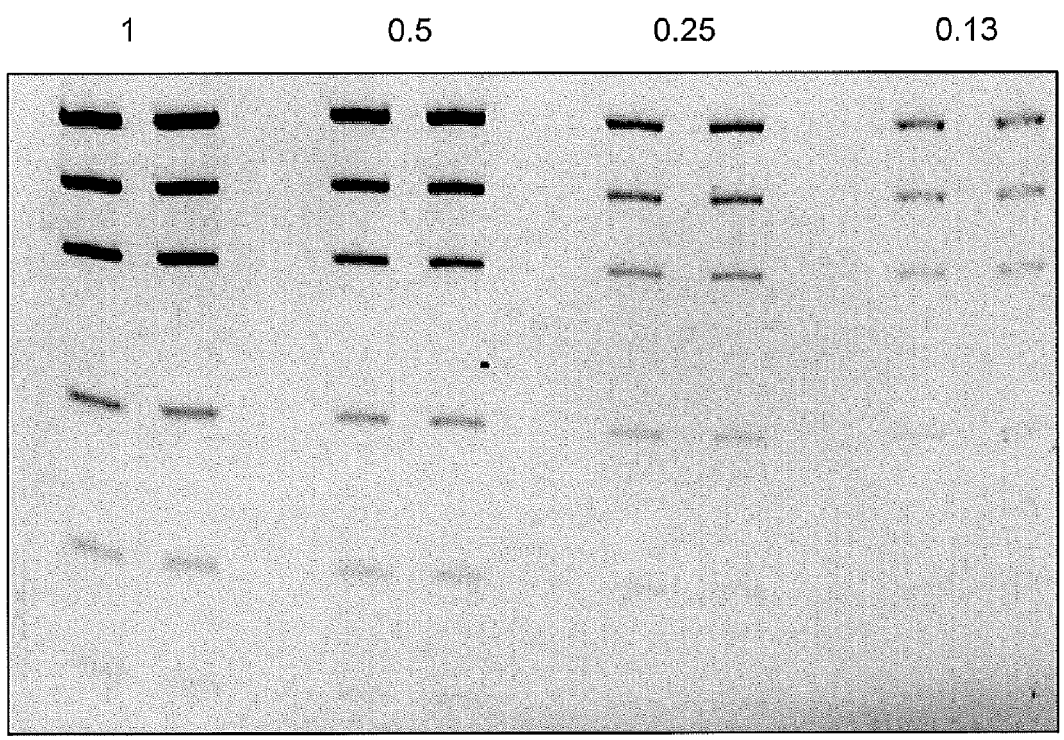
Figure 4E:
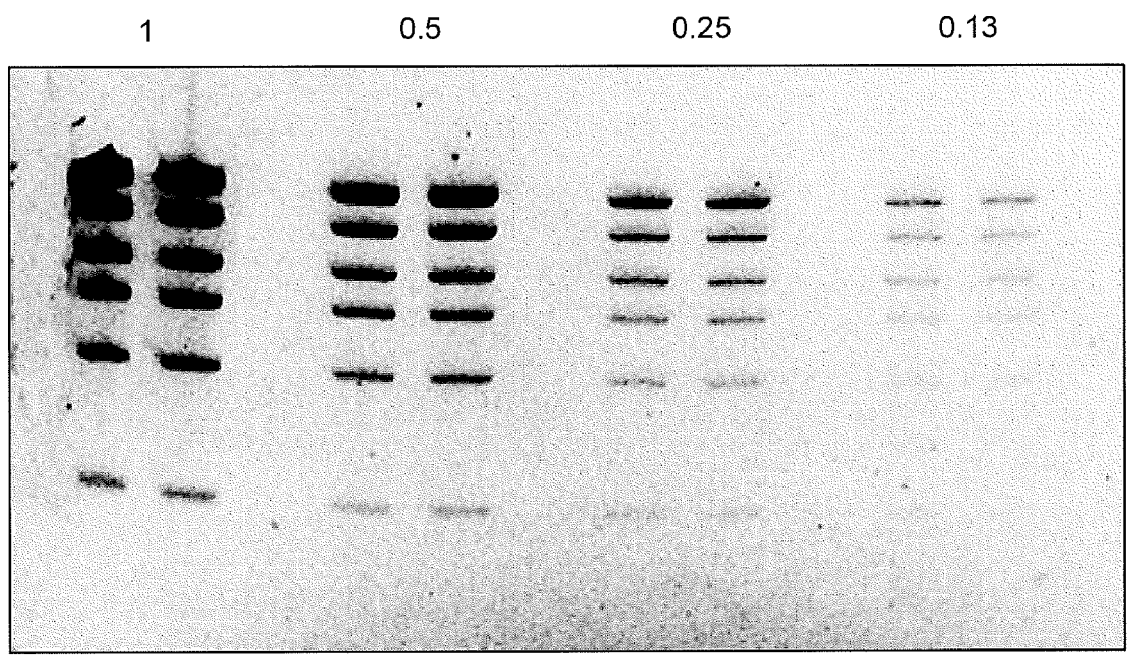
Figure 4F:
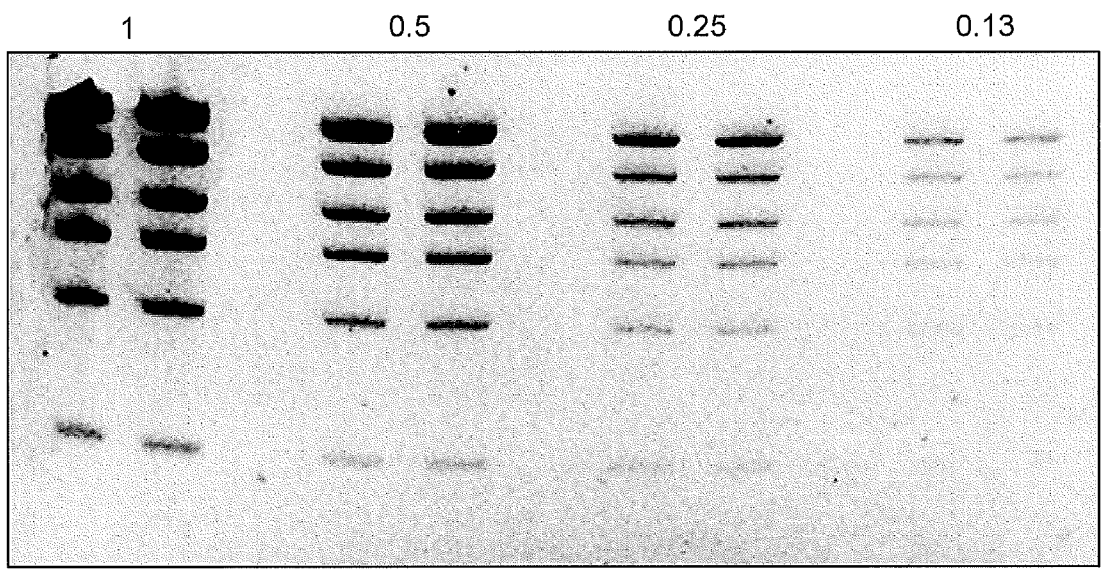

The number of revertants was counted and the test compounds were either considered non-mutagenic or mutagenic. The criteria for determining if a test compound was mutagenic was based on a 2-fold increase in mean revertants per plate for at least one tester strain (TA97a, TA98, TA100 and TA102) over the mean revertants per plate of the appropriate vehicle control. For tester strains TA1535, TA1537 and TA 1538 a positive mutant was identified by a 3-fold increase in mean revertants per plate compared to the appropriate vehicle control. In addition, the increase in the mean number of revertants per plate needed to be accompanied by a dose response to increasing concentrations of the test compound. Based on this scoring methodology, in the presence of S9, Compound 1 was considered mild or non-mutagenic for all tester strains wherein Compound 1 demonstrated between a 3- and 4-fold increase in revertants for four of the tester strains, thiazole orange was considered mutagenic in the presence of S9 with five of the tester strains and ethidium bromide was considered mutagenic for three of the tester strains demonstrating a 4- to 80-fold increase in revertants for four of the tester strains, See FIG. 2 and Table 1. Thiazole orange was also considered mutagenic for two of the tester strains in the absence of S9. Thus, compared to ethidium bromide, thiazole orange is 3-4 times less mutagenic and Compound 1 is 4-5 times less mutagenic. Ethidium bromide and Sybr Green I had previously been tested wherein Sybr Green I was considered a weak mutagen (Singer et al. Mutation Research 439 (1999) 37-47).

TABLE 2

| | TA97a | TA98 | TA100 | TA102 | TA1535 | TA1537 | TA1538 |
|---|---|---|---|---|---|---|---|
| | \multicolumn{7}{c}{increase in revertants compared to vehicle control (DMSO)} |
| Ethidium bromide | 4.4 | 68.0 | 1.6 | 2.0 | 1.4 | 15 | 80 |
| Thiazole orange | 6.9 | 6.4 | 2.2 | 4.7 | 1.5 | 17.4 | 7.8 |
| Compound 1 | 3.3 | 3.0 | 1.7 | 3.7 | 1.8 | 1.8 | 3.7 |

Example 3

In Vitro Transformation of Syrian Hamster Embryo (SHE) Cells by 7-Day Exposure Screening Assay This assay design is based on procedures described by Kerchaert et al Mutation Research 356 (1996) 65-84, and is an accepted method for evaluating the carcinogenic potential of chemical substances. Thus, the objective of the assay was to determine the ability of the test compounds (Ethidium bromide, thiazole orange and Compound 1) for inducing an increase in morphological transformation of cultured Syrian hamster embryo cells, relative to vehicle control cultures, following a 7-day exposure period.

SHE cell cultures were grown in LeBoeuf's modification (0.75 g/L NaHCO3, pH 6.65-6.75) of Dulbecco's Modified Eagle Medium (DMEM) supplemented with 20% fetal bovine serum (FBS) and 4 mM L-glutamine. The cultures were maintained at 37±1° C. in an atmosphere of 10±0.5% $CO_2$ in humidified air. The known procarcinogen, benzo[a]pyrene (B[a]P) was used as a positive control, dissolved in DMSO and used at a concentration range of 1.25 to 5 μg/ml in the SHE cell cultures. The final concentration of DMSO in the cell cultures was about 0.2%. The test compounds were dissolved in DMSO and used at a final concentration range of 0.0400 to 0.800 μg/ml in the SHE cell cultures. After the 7-day incubation period, the culture dishes were washed in Hanks' balanced salt solution (HBSS), fixed with methanol, and stained with 10% buffered aqueous Giemsa. After washing with tap water the dishes were air-dried. The average number of colonies per dish were determined and for each dose group, the average relative plating efficiency (relative survival, RPE) was calculated, relative to the vehicle control group. The criteria applied to identifying colonies showing the morphologically transformed phenotype was 1) colonies possessing piled-up cells with random orientation (crisscrossing) of the 3-dimensional growth, 2) colonies with crisscross cells and increased cytoplasmic basophilia throughout the colony, and/or 3) colonies containing cells with decreased cytoplasm:nucleus ratios compared to normal SHE cells.

The test compounds were evaluated as positive in this assay if they caused a statistical significant increase in morphological transformation frequency for at least two dose levels compared to concurrent vehicle control or if one dose showed a statistically significant increase and the trend test was significant. The test compounds were evaluated as negative if no statistically significant increase in morphological transformation was obtained. Based on this methodology, Compound 1 was considered negative while Thiazole orange and ethidium bromide were both considered positive in the screening SHE cell transformation assay under 7-day exposure conditions.

Specifically, Compound 1 was essentially noncytotoxic at 0.0500 μg/mL (120% RPE), slightly cytoxic at 0.150 μg/mL (88% RPE) and moderately cytotoxic at 0.300 μg/mL (59% RPE) wherein none of the three treatment groups induced a significant increase in the frequency of morphological transformation compared to the concurrent vehicle control.

TABLE 3

| Treatment group | MT Frequency (%) | RPE |
|---|---|---|
| Vehicle control (DMSO) | 0.106 | 100% |
| Positive Control | 1.553 | 114% |
| Compound 1 | | |
| 0.0500 μg/mL | 0.442 | 120% |
| 0.150 μg/mL | 0.315 | 88% |
| 0.300 μg/mL | 0.144 | 59% |

MT = morphologically transformed;
RPE = relative plating efficiency

Thiazole orange was essentially noncytotoxic at 0.0400 μg/mL (97% RPE), moderately cytotoxic at 0.150 μg/mL (52% RPE) and highly toxic at 0.260 μg/mL (25% RPE) wherein two of the three treatment groups, 0.0400 and 0.150 μg/mL, induced significant increases in frequency of morphological transformation compared to concurrent vehicle control.

TABLE 4

| Treatment group | MT Frequency (%) | RPE |
|---|---|---|
| Vehicle control (DMSO) | 0.059 | 100% |
| Positive Control | 1.443 | 86% |
| Compound 1 | | |
| 0.0400 μg/mL | 0.731 | 97% |
| 0.150 μg/mL | 0.852 | 52% |
| 0.260 μg/mL | 0.294 | 25% |

MT = morphologically transformed;
RPE = relative plating efficiency

Ethidium bromide was slightly cytotoxic at 0.200 μg/mL (85% RPE), moderately cytotoxic at 0.400 μg/mL (66% RPE) and highly cytotoxic at 0.800 μg/mL (28% RPE). Two of the three treatment groups, 0.400 and 0.800 μg/mL, induced significant increases in the frequency of morphological transformation compared to the concurrent vehicle control.

TABLE 5

| Treatment group | MT Frequency (%) | RPE |
|---|---|---|
| Vehicle control (DMSO) | 0.059 | 100% |
| Positive Control | 1.443 | 86% |
| Compound 1 | | |
| 0.200 μg/mL | 0.313 | 85% |
| 0.400 μg/mL | 1.304 | 66% |
| 0.800 μg/mL | 0.635 | 28% |

MT = morphologically transformed;
RPE = relative plating efficiency

Example 4

L5178Y TK+/− Mouse Lymphoma Forward Mutation Screen

This assay evaluated the test compounds for their ability induce significant mutagenic activity at the thymidine kinase (TK) locus in L5178Y mouse lymphoma cells as assayed by colony growth in the presence and absence of S9, an exogenous metabolic activation system of mammalian microsomal enzymes derived from Acrolor-induced rat liver and is based on the assay reported by (Clive and Spector, 31 Mutation Research (1975) 17-29; Clive et al. 59 Mutation Research (1979) 61-108; Amacher et al Mutation Research 72 (1980) 447-474; Clive et al. Mutation Research 189 (1987) 143-156). The cell cultures were scored for both cytotoxicity and increases in the mutant frequency wherein a positive result was based on a frequency that was at least twice the average mutant frequency of the concurrent vehicle control (DMSO). The mouse lymphoma cells used for this assay were heterozygous at the TK locus and may undergo a single step forward mutation to the $TK^{-/-}$ genotype in which little or no TK activity remains. These mutants are viable in normal cell culture medium but these mutants are resistant to the thymidine analog 5-trifluorothymidine (TFT) because they cannot incorporate the toxic analog of thymidine into DNA. Thus, cells that grow to form colonies in the presence of TFT are therefore assumed to have mutated, either spontaneously or by the test compounds. The results of this assay are not definitive but rather an indicator that a test compound has mutagenic properties, or not.

The mouse lymphoma cells were cultured in RPMI 1640 supplemented with horse serum (10% by volume), Pluronic F68, L-glutamine, sodium pyruvate, penicillin and streptomycin (Amacher et al Mutation Research 72 (1980) 447-474; Clive and Spector, Mutation Research 31 (1975) 17-29). Treatment medium was Fisher's medium with the same medium supplements as used for the culture medium except that the horse serum was reduced to 5% by volume. Cloning medium was RPMI 1640 with up to 20% horse serum, without Pluronic F68 and with the addition of 0.24% BBL agar to achieve a semisolid state. Selection medium was cloning medium containing 3 µg/ml of TFT (Clive et al. Mutation Research 189 (1987) 143-156).

The positive controls were Methyl methanesulfonate (MMS) and Methylcholanthrene (MCA) to be used without and with the S9 activation, respectively. MMS is a direct acting mutagen that is highly mutagenic to L5178Y $TK^{+/-}$ cells and was used at a concentration of 13 µg/mL. MCA requires metabolic activation by microsomal enzymes to become mutagenic to L5178Y $TK^{+/-}$ cells, S9, and was used at a concentration of 2 and/or 4 µg/mL. The test compounds, ethidium bromide, thiazole orange and Compound 1, were assayed at concentrations of 0.00625 to 4.93 µg/mL.

The cells were pelleted and resuspended in treatment medium containing controls or test compounds, with and without S9. The tubes were placed in an orbital shaker incubator at 35-38° C. and rotated at 70±10 orbitals per minute. After a four-hour exposure period the cells were washed twice, resuspended in 10 mL of culture medium and returned to the orbital shaker and the cells were allowed to grow for two days for mutant recovery. Cell densities less than approximately $3 \times 10^5$ cells/mL after day 2 were no considered for mutant selection. The mutants were recovered by plating a total of $3 \times 10^6$ cells in selection medium in soft agar. The dishes were incubated for 10 to 14 days at approximately 37° C. with about 5% $CO_2$/95% humidified air.

The mutant frequency was calculated as the ratio of the total number of mutant colonies found in each mutant selection dishes to the total number of cells seeded, adjusted by the absolute selection cloning efficiency. The cytotoxicity was based on the relative suspension growth of cells over the 2-day expression period multiplied by the relative cloning efficiency at the time of selection resulting in a relative total growth (RTG) number. Based on this methodology, all three test compounds were considered non-mutagenic but with possessing varying degrees of cytotoxicity.

Specifically, ethidium bromide, without S9 in the treatment medium, was weakly cytotoxic at 0.620 µg/mL, moderately cytotoxic at 2.47 µg/mL and moderately high cytotoxic at 4.93 µg/mL. These concentrations demonstrated no increase in the mutant frequency that exceeded the minimum criterion, 2-fold increase compared to the concurrent vehicle control. Ethidium bromide, with S9 in the treatment medium, was moderately cytotoxic at 2.47 µg/mL (37.1% RTG) and moderately high cytotoxic at 4.93 µg/mL (23.1% RTG). No increases in the mutation frequency were observed that exceeded the minimum criterion.

TABLE 6

| | Without S9 | | With S9 | |
|---|---|---|---|---|
| Treatment Group | RTG % | Mutant Frequency ($\times 10^{-6}$ Units) | RTG % | Mutant Frequency ($\times 10^{-6}$ Units) |
| Vehicle control (DMSO) | 99.7 | 57.3 | 98 | 49.2 |
| Positive Control (MMS 13 µg/mL) | 22.4 | 425.6 | N/A | N/A |
| Positive Control (MCA 2 µg/mL) | N/A | N/A | 35.0 | 446.4 |
| Positive Control (MCA 4 µg/mL) | N/A | N/A | 17.1 | 478.4 |
| Test Compound | | | | |
| .620 µg/mL | 53.6 | 64.3 | N/A | N/A |
| 1.24 µg/mL | 46.3 | 59.3 | N/A | N/A |
| 2.47 µg/mL | 33.7 | 67.6 | 37.1 | 73.7 |
| 4.93 µg/mL | 22.7 | 94.2 | 23.1 | 93.6 |

Compound 1 without S9 was noncytoxic at 0.125 µg/mL (80.3% RTG) and moderately high cytotoxic at 0.250 µg/mL (26.5% RTG). No increases in the mutant frequency were observed that exceeded twice the frequency of the concurrent vehicle control. With S9, Compound 1 was weakly cytotoxic at 1.24 µg/mL (65.1% RTG), moderately cytotoxic at 2.47 µg/mL (47.1% RTG) and was excessively cytotoxic at 4.93 µg/mL (7.6% RTG). No increases in the mutation frequencies were observed that were twice the frequency of the concurrent vehicle control.

TABLE 7

| | Without S9 | | With S9 | |
|---|---|---|---|---|
| | RTG % | Mutant Frequency ($\times 10^{-6}$ Units) | RTG % | Mutant Frequency ($\times 10^{-6}$ Units) |
| Vehicle control | 100.5 | 49.0 | 98 | 72.6 |
| Positive Control (MMS 13 µg/mL) | 27 | 311.6 | N/A | N/A |
| Positive Control (MCA 2 µg/mL) | N/A | N/A | 35.0 | 446.4 |

TABLE 7-continued

| | Without S9 | | With S9 | |
|---|---|---|---|---|
| | RTG % | Mutant Frequency ($\times 10^{-6}$ Units) | RTG % | Mutant Frequency ($\times 10^{-6}$ Units) |
| Positive Control (MCA 4 μg/mL) | N/A | N/A | 17.1 | 478.4 |
| Test Compound | | | | |
| 0.125 μg/mL | 80.3 | 55.2 | N/A | N/A |
| 0.250 μg/mL | 26.5 | 67.3 | N/A | N/A |
| 1.24 μg/mL | N/A | N/A | 65.1 | 70.6 |
| 2.47 μg/mL | N/A | N/A | 47.1 | 86.7 |
| 4.93 μg/mL | N/A | N/A | 7.6 | 114.5 |

Thiazole orange, without S9, was weakly cytotoxic at 0.100 μg/mL (60.9% RTG) and moderately cytotoxic at 0.200 μg/mL (23.4% RTG). No increases in mutation frequency were observed that were twice the frequency of the concurrent vehicle control. With S9, thiazole orange was noncytotoxic at 4.93 μg/mL (90.4% RTG) and moderately high cytotoxic at 9.85 μg/mL (22.6% RTG). No increases in the mutant frequency were observed that were twice the frequency of the concurrent vehicle control.

TABLE 8

| | Without S9 | | With S9 | |
|---|---|---|---|---|
| Treatment Group | RTG % | Mutant Frequency ($\times 10^{-6}$ Units) | RTG % | Mutant Frequency ($\times 10^{-6}$ Units) |
| Vehicle control | 100.5 | 49.0 | 98 | 72.6 |
| Positive Control (MMS 13 μg/mL) | 27 | 311.6 | N/A | N/A |
| Positive Control (MCA 2 μg/mL) | N/A | N/A | 35.0 | 446.4 |
| Positive Control (MCA 4 μg/mL) | N/A | N/A | 17.1 | 478.4 |
| Test Compound | | | | |
| 0.100 μg/mL | 60.9 | 53.0 | N/A | N/A |
| 0.200 μg/mL | 23.4 | 58.8 | N/A | N/A |
| 4.93 μg/mL | N/A | N/A | 90.4 | 77.4 |
| 9.85 μg/mL | N/A | N/A | 22.6 | 78.0 |

Example 5

Screening Assay for Chromosomal Aberrations in Cultured Human Peripheral Blood Mononuclear Cells (PBMC)

The objective of this assay was to evaluate the ability of the test compounds, ethidium bromide, thiazole orange and Compound 1, to cause structural chromosomal aberrations in cultured human lymphocytes with and without exogenous metabolic activation system. Human venous blood from healthy adult volunteers was drawn in heparinized vacutainers. The whole blood cultures were initiated in 15 ml centrifuge tubes by adding approximately 0.3 ml of fresh heparinized blood into a sufficient volume of culture medium, to that the final volume was 5 mL in the assay with and without metabolic activation after the addition of the test compound. The culture medium was RPMI 1640 supplemented with approximately 20% heat-inactivated fetal bovine serum (FBS), penicillin (100 units/mL), streptomycin (100 μg/mL), L-glutamine (2 mM) and 2% phytohemagglutinin M (PHA-M). The cultures were incubated with loose caps at 37° C.±2° C. in a humidified chamber of approximately 5% CO2 in air.

The positive controls were Mitomycin C (MMC) and cyclophosphamide (CP) to be used without and with the S9 activation, respectively. MMC is a direct acting clastogen that does not require metabolic activation and was used at a concentration of 0.025 to 3.0 μg/mL. CP requires metabolic activation by microsomal enzymes to become converted to a clastogenic intermediate, and was used at a concentration of 10 to 300 μg/mL. The test compounds, ethidium bromide, thiazole orange and Compound 1, were assayed at concentrations of 0.500 to 10 μg/mL. The in vitro metabolic activation system consisted of a rat liver post-mitochondrial fraction (S9) and an energy-producing system (NADPH plus isocitric acid) (Maron and Ames, 113 Mutation Research (1983) 173-215).

Two days after culture initiation, the cultures were treated with the test compounds. The cultures without the S9 metabolic activation mixture were incubated for an additional 22 hours with Colcemid (0.1 μg/mL) added for the last 2±0.5 hours. The cultures with the S9 metabolic activation mixture were incubated for a 3-hour exposure period. After exposure the cells were washed at least twice with PBS, and fresh culture medium added. The cell culture was then incubated for an additional 18 hours, with Colcemid (0.1 μg/mL) added for the last 2±0.5 hours of incubation.

At the end of the incubation period the cultures were centrifuged, the supernatant discarded, and the cells swollen with 75 mM KCl, fixed in methanol:glacial acetic acid (3:1 v/v), dropped onto glass slides and air dried. The slides were stained with 5% Giemsa and air dried and then analyzed for mitotox index, chromosomal aberrations including polyploidy and endoreduplication. Based on this methodology, the cells individually treated with the three test compounds, with and without the S9 activation mixture, showed no significant increase in the number of cells with structural aberrations, polyploidy or endoreduplication compared to the concurrent vehicle control. Thus, ethidium bromide, thiazole orange and Compound 1 were considered negative for inducing structural chromosomal aberrations with and without metabolic activation.

Example 6

Comparison of Ethidium and Compound 1 Staining of Nucleic Acid Separated and Immobilized in an Agarose Gel Different concentrations of DNA (62.5 ng, 31.25 ng, 15.63 ng, 7.813 ng, 3.906 ng, 1.953 ng, 976.6 pg, 488.3 pg, 244.1 pg, 122.1 pg, 61.04 pg and 30.52 pg) were loaded and separated on a 1% agarose gel at 60 v in 0.5×TBE. The gels were stained with a staining solution comprising TBE (50 mL) and either ethidium bromide (2.5 μl of stock solution, 10 mg/mL in water) or compound 1 (5 μl of dye stock solution in DMSO for a final concentration of 1 μM) for 30, 60 and 90 minutes. All gels were subsequently photographed. These gels demonstrate that Compound 1 is at least as sensitive as ethidium bromide for detection nucleic acid in a gel using similar staining procedures.

Example 7

Hazardous Waste Screening Test

Compound 1 was tested to determine whether or not the compound was hazardous or toxic to aquatic life. Ten fathead minnows (*Pimephakes promelas*) were placed each in a 8 liter tank containing vehicle control and a concentration of Compound 1 at 250 mg/L, 500 mg/L and 750 mg/L. After a 96 hour exposure period the number of viable minnows were counted. The survival rate of the minnows for the control and Compound 1 was 100%. Thus, compound 1 has a $LC_{50}$ value >500 mg/L, which is classified as not hazardous under CCR Title 22 acute toxicity to aquatic life.

Example 8

Cell Permeability of Compound 1 on Live Eukaryotic Cells

MRC5 human lung fibroblast cells were harvested and grown in complete culture media (DMEM+10% FBS) for one day after seeding coverslips. Cells were then removed from complete media and placed in Hank's balanced salt solution w/sodium bicarbonate (HBSS) supplemented with 5 mM HEPES, 100 uM L-glutamine and 100 uM succinate containing varying concentrations of Compound 1. Concentrations tested included 0.5, 1.0, 5.0 and 10.0 µM. Cells were incubated for 5 minutes at 37° C./5% CO2. Cells were washed 3×30 seconds in HBSS and mounted on microscope slides in HBSS and sealed with paraffin. After mounting, slides were examined on a Nikon Eclipse 800 upright fluorescent microscope and imaged with standard FITC and TRITC filter sets, a Princeton Instrument MicroMax cooled CCD camera, and Universal Imaging MetaMorph imaging software. Compound 1 appears to be cell permeable in live MRC5 cells. Labeling pattern appears to be nuclear and cytoplasmic with prominent signal in the nucleolus of labeled cells. Signal associated with Compound 1 is detectable with both FITC and TRITC filter sets with greater signal intensity using the FITC set. Regardless of concentration, nucleolar labeling seems to be the most prominent and appears to become slightly more prominent at lower concentrations. Off cell background was minimal in all cases.

Example 9

Detection of DNA in an Agarose Gel with Compound 1

Different quantities of the Low DNA Mass Ladder 1 µl, 0.5 µl, 0.25 µl, 0.13 µl, (Invitrogen Corp. Cat # 10068-013) were loaded on an E-Gel 2% (Invitrogen), prepared according to the description in U.S. Pat. No. 5,582,702 where the Ethidium Bromide has been replaced by a 4× concentration of Compound 1 from a 10000× solution. The gels were run using the Powerbase (Invitrogen, Cat # G6200-04) for 30 minutes, then visualized using the Clare Chemical Dark Reader. See, FIG. 4.

Example 10

EPA Acute Oral Toxicity Test for Compound 1 in 0.5×TBE

A Limit Screen test was performed according to OPPTS guidelines (870.1100) using three female Sprague Dawley rats, which received an oral Limit Dose of 5000 mg/kg of the test article. The animals were observed for mortality, weight change and toxic signs for a two week period.

Since all three rats survived for two weeks after the dose administration, the $LD_{50}$ for the test article was considered to be greater than the limit dose and no additional testing was required.

All animals were euthanized at the termination of the study. Gross necropsies were performed and no abnormalities were observed in any of the test animals.

Example 11

NPDES (National Pollutant Discharge Elimination System) Testing for Compliance with the Clean Water Act Compound 1 complies with the Clean Water Act and the National Pollutant Discharge Elimination System regulations, as it does not contain cyanide, phenolics, pollutant metals, organochlorine pesticides, PCBs, or semi-volatile or volatile organic compounds. The testes were performed according to EPA protocols cited in Table 9.

TABLE 9

| Analysis (EPA method, as per 40 CFR part 136) | Compound 1 in 0.5X TBE | 0.5X TBE |
|---|---|---|
| pH (150.1) | 8.45 | 8.48 |
| Total Cyanide (335.2) | None | None |
| BOD (405.1) | None | None |
| COD (410.1) | 7020 | 6840 |
| Ammonia as Nitrogen (350.1) | 253 | 248 |
| Total Organic Carbon (415.1) | 2480 | 2360 |
| Total Phenolics (420.1) | None | None |
| Organochlorine Pesticides and PCBs (608M) | None | None |
| Semi-volatile Organic Compounds (625) | None | None |
| Volatile Organic Compounds (624) | None | Chloroform (17 ug/L) |
| Metals (Sb, As, Be, Cd, Cr, Cu, Pb, Hg, Ni, Se, Ag, Tl, Zn) (6010B, 7060A, 7421, 7470A, 7740, 7841) | None | None |

Example 12

Synthesis of Compound 1

A mixture of 33.92 g of lepidine and 50.45 g of propyl tosylate is heated at 110 C for 1 hour. The reaction is cooled to room temperature and 600 mL of ethyl acetate is added and heated at 60 C for 1 hour. The mixture is filtered and 75.75 g of the intermediate 4-methyl-1-propylquinolinium tosylate is obtained. The intermediate is mixed with 78.05 g of 3-methyl-2-methylthiobenzothiazolium tosylate in 300 mL of methylene chloride and 64.53 g of triethylamine is introduced. The reaction mixture is stirred at room temperature overnight and 1 L of ethyl acetate is then added and the product is filtered.

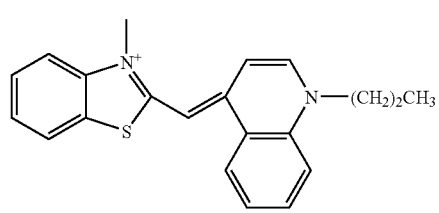

Compound 1

The preceding examples can be repeated with similar success by substituting the specifically described nucleic acid dye compounds of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

All patents and patent applications mentioned in this specification are herein incorporated by reference to the same extent as if each individual publication, patent or patent application was specifically and individually indicated to be incorporated by reference.

What is claimed is:

1. A method for determining the presence or absence of nucleic acid in a sample, wherein the method comprises:
   a) combining an unsymmetrical cyanine dye compound with a sample to prepare a labeling mixture, wherein the sample is immobilized on a solid or semi-solid support and the unsymmetrical cyanine dye compound has the formula

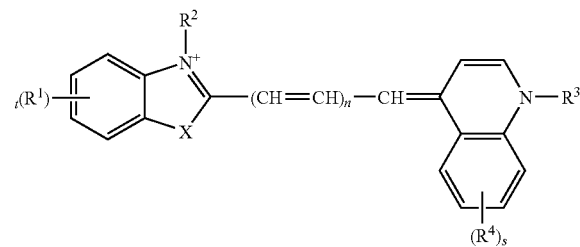

wherein X is S or $C(CH_3)_2$;
   $R^1$ is a fused benzene, methoxy, a $C_1$-$C_6$ alkyl;
   $R^2$ and $R^3$ are independently a $C_1$-$C_6$ alkyl;
   $R^4$ is a $C_1$-$C_6$ alkyl or a methoxy;
   t is independently 0, 1, 2, 3, or 4;
   s is independently 0, 1, 2, 3 or 4 and
   n is 0, 1, 2 or 3;
   b) incubating the labeling mixture for a sufficient amount of time for the unsymmetrical cyanine dye compound to associate with the nucleic acid to prepare an incubated sample;
   c) illuminating the incubated sample with an appropriate wavelength to prepare an illuminated sample; and
   d) observing the illuminated sample whereby the presence or absence of the nucleic acid is determined,
   wherein the unsymmetrical cyanine dye compound is combined with the sample before the sample is immobilized, and wherein the nucleic acid is a combination of DNA and RNA,
   with the proviso that the unsymmetrical cyanine dye compound is not thiazole orange when the support is a polymeric gel.

2. The method according to claim 1, wherein the nucleic acid is a combination of single stranded RNA, double stranded RNA, single stranded DNA, and double stranded DNA.

3. The method according to claim 1, wherein the DNA is single stranded DNA or double stranded DNA.

4. The method according to claim 1, wherein the RNA is single stranded RNA or double stranded RNA.

5. The method according to claim 1, wherein the solid or semi solid support is a polymeric gel, a membrane, an array, a glass bead, a glass slide, or a polymeric microparticle.

6. The method according to claim 1, wherein the solid or semi-solid support is agarose or polyacrylamide gel.

7. The method according to claim 1, wherein the unsymmetrical cyanine dye compound is immobilized on a polymeric membrane.

8. The method according to claim 1, wherein the cyanine dye has formula

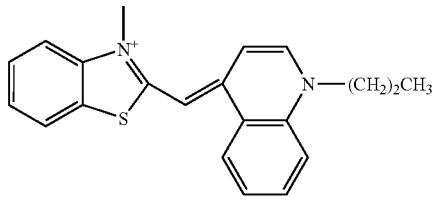

and is characterized as being essentially non-genotoxic in eukaryotic cells.

9. The method according to claim 1, wherein the nucleic acid is a combination of single stranded RNA, double stranded RNA, single stranded DNA, and double stranded DNA that is immobilized on an agarose or polyacrylamide gel.

10. The method according to claim 1, wherein the DNA is single stranded DNA or double stranded DNA that is immobilized on an agarose or polyacrylamide gel.

11. The method according to claim 1, wherein the RNA is single stranded RNA or double stranded RNA that is immobilized on an agarose or polyacrylamide gel.

* * * * *